United States Patent
Myoba et al.

(10) Patent No.: US 11,913,955 B2
(45) Date of Patent: Feb. 27, 2024

(54) METHODS FOR DETECTING CANCERS, AND DETECTING REAGENT

(71) Applicant: TOSOH CORPORATION, Shunan (JP)

(72) Inventors: Shohei Myoba, Ayase (JP); Norihisa Ohtake, Ayase (JP)

(73) Assignee: TOSOH CORPORATION, Shunan (JP)

(*) Notice: Subject to any disclaimer, the term of this patent is extended or adjusted under 35 U.S.C. 154(b) by 711 days.

(21) Appl. No.: 16/643,381

(22) PCT Filed: Aug. 22, 2018

(86) PCT No.: PCT/JP2018/030916
§ 371 (c)(1),
(2) Date: Feb. 28, 2020

(87) PCT Pub. No.: WO2019/044602
PCT Pub. Date: Mar. 7, 2019

(65) Prior Publication Data
US 2020/0256872 A1    Aug. 13, 2020

(30) Foreign Application Priority Data
Aug. 30, 2017 (JP) ................................. 2017-165409

(51) Int. Cl.
*G01N 33/574* (2006.01)
*G01N 33/68* (2006.01)

(52) U.S. Cl.
CPC ....... *G01N 33/574* (2013.01); *G01N 33/6848* (2013.01)

(58) Field of Classification Search
CPC ........... G01N 33/574; G01N 33/57488; G01N 33/6848; C07K 14/475; C07K 16/22
See application file for complete search history.

(56) References Cited

U.S. PATENT DOCUMENTS

| | | |
|---|---|---|
| 2004/0053325 A1 | 3/2004 | Breit et al. |
| 2009/0004181 A1 | 1/2009 | Breit |
| 2010/0159608 A1 | 6/2010 | Hess et al. |
| 2011/0033886 A1 | 2/2011 | Hess et al. |
| 2011/0065204 A1 | 3/2011 | Wollert et al. |
| 2011/0263443 A1 | 10/2011 | Hess et al. |
| 2017/0010280 A1 | 1/2017 | Tanaka et al. |
| 2021/0190786 A1* | 6/2021 | Arakawa .......... G01N 33/57434 |

FOREIGN PATENT DOCUMENTS

| | | | |
|---|---|---|---|
| CN | 101852804 A | 10/2010 | |
| EP | 3425392 A1 | 1/2019 | |
| JP | 2003-532079 A | 10/2003 | |
| JP | 2009-545735 A | 12/2009 | |
| JP | 2010-528275 A | 8/2010 | |
| JP | 2011-523051 A | 8/2011 | |
| JP | 2011-190262 A | 9/2011 | |
| JP | 2012-515335 A | 7/2012 | |
| KR | 10-2005-0076377 A | 7/2005 | |
| WO | 2011/102461 A1 | 8/2011 | |
| WO | 2015/108077 A1 | 7/2015 | |
| WO | WO-2017150314 A1 * | 9/2017 | ........... C07K 14/475 |

OTHER PUBLICATIONS

Van Belzen et al., Precision Oncology, 2021, 5(15), 1-11. (Year: 2021).*
Bauskin et al., The EMBO Journal, 2000, 19(10):2212-2220.*
Jemura et al. Journal of Clinical Oncology, (Feb. 2017) vol. 35, No. 6, Supp. Supplement 1, abstract.*
Jemura et al., Cancer Research, (Jul. 2017) vol. 77, No. 13, Supp. Supplement 1. Abstract No. 228.*
Uemura et al. Journal of Clinical Oncology, (Feb. 2017) vol. 35, No. 6, Supp. Supplement 1, abstract.*
Uemura et al., Cancer Research, (Jul. 2017) vol. 77, No. 13, Supp. Supplement 1. Abstract No. 228.*
English translation of International Preliminary Report on Patentability with translation of Written Opinion dated Mar. 3, 2020, in International Application No. PCT/JP2018/030916.
Communication dated Apr. 8, 2021, from the European Patent Office in counterpart European Application No. 18850267.8.
Asne R. Bauskin et al., "The TGF-β Superfamily Cytokine MIC-1/GDF15: Secretory Mechanisms Facilitate Creation of Latent Stromal Stores", Journal of Interferon & Cytokine Research, vol. 30, No. 6, 2010, pp. 389-397 (10 Pages Total).
P. Vaňhara, et al., "Growth/differentiation factor-15: prostate cancer suppressor or promoter?" Prostate Cancer and Prostatic Diseases, 2012, pp. 320-328, vol. 15.
Asne R. Bauskin, et al., "The Propeptide Mediates Formation of Stromal Stores of PROMIC-1: Role in Determining Prostate Cancer Outcome", Cancer Res., 2005, pp. 2330-2336, vol. 65, No. 6.

(Continued)

*Primary Examiner* — Hong Sang

(74) *Attorney, Agent, or Firm* — Sughrue Mion, PLLC

(57) ABSTRACT

The present invention provides a method for detecting cancer in a simple and highly accurate manner, and a reagent that can be used in the method. According to the present invention, cancer (excluding castration-resistant prostate cancer) is detected by measuring the intact growth and differentiation factor (GDF15) propeptide level, the GDF15 propeptide fragment level, or the total of the intact GDF15 propeptide level and the GDF15 propeptide fragment level, in a sample. The above described method for detecting cancer includes a method for detecting one or more selected from the group consisting of stomach cancer, pancreatic cancer, colorectal cancer, lung cancer, breast cancer and esophageal cancer, and a method for distinguishing and detecting non-small cell lung cancer and small cell lung cancer. Further, a reagent for detecting cancer includes an antibody that specifically recognizes GDF15 propeptide.

9 Claims, 10 Drawing Sheets

Specification includes a Sequence Listing.

(56) References Cited

OTHER PUBLICATIONS

Xingya Wang, et al., "The diverse roles of nonsteroidal anti-inflammatory drug activated gene (NAG-1/GDF15) in cancer", Biochemical Pharmacology, 2013, pp. 597-606, vol. 85.

David A. Brown, et al., "Macrophage Inhibitory Cytokine 1: A New Prognostic Marker in Prostate Cancer", Clin Cancer Res., 2009, pp. 6658-6664, vol. 15, No. 21.

Anne Cathrine Staff, et al., "Elevated Plasma Growth Differentiation Factor-15 Correlates with Lymph Node Metastases and Poor Survival in Endometrial Cancer", Clinical Cancer Research, Jul. 2011, pp. 4825-4833, vol. 17, No. 14.

David A. Brown, et al., "MIC-1 Serum Level and Genotype: Associations with Progress and Prognosis of Colorectal Carcinoma", Clinical Cancer Research, Jul. 2003, pp. 2642-2650, vol. 9.

Jens Koopmann, et al., "Serum Markers in Patients with Resectable Pancreatic Adenocarcinoma: Macrophage Inhibitory Cytokine 1 versus CA19-9", Clin Cancer Res., Jan. 15, 2006, pp. 442-446, vol. 12, No. 2.

Xiaobing Wang, et al., "Macrophage inhibitory cytokine 1 (MIC-1/GDF15) as a novel diagnostic serum biomarker in pancreatic ductal adenocarcinoma", BMC Cancer, 2014, pp. 578-588, vol. 14.

International Search Report for PCT/JP2018/030916 dated Nov. 27, 2018 [PCT/ISA/210].

Written Opinion for PCT/JP2018/030916 dated Nov. 14, 2018 [PCT/ISA/237].

Office Action dated Aug. 22, 2023 issued by the Chinese Patent Office in Chinese Application No. 201880054905.3.

Communication dated Sep. 5, 2023 issued by the European Patent Office in European Application No. 18 850 267.8.

\* cited by examiner

SEQUENCE LISTING

<160> NUMBER OF SEQ ID NOS: 8

<210> SEQ ID NO 1
<211> LENGTH: 1220
<212> TYPE: DNA
<213> ORGANISM: Homo sapiens
<220> FEATURE:
<221> NAME/KEY: CDS
<222> LOCATION: (33)..(956)

<400> SEQUENCE: 1

```
agtcccagct cagagccgca acctgcacag cc atg ccc ggg caa gaa ctc agg        53
                                    Met Pro Gly Gln Glu Leu Arg
                                    1               5 acg gtg aat ggc tct cag atg ctc ctg gtg ttg ctg gtg ctc tcg tgg       101
Thr Val Asn Gly Ser Gln Met Leu Leu Val Leu Leu Val Leu Ser Trp
            10                  15                  20 ctg ccg cat ggg ggc gcc ctg tct ctg gcc gag gcg agc cgc gca agt       149
Leu Pro His Gly Gly Ala Leu Ser Leu Ala Glu Ala Ser Arg Ala Ser
        25                  30                  35 ttc ccg gga ccc tca gag ttg cac tcc gaa gac tcc aga ttc cga gag       197
Phe Pro Gly Pro Ser Glu Leu His Ser Glu Asp Ser Arg Phe Arg Glu
40                  45                  50                  55
```

```
ttg cgg aaa cgc tac gag gac ctg cta acc agg ctg cgg gcc aac cag    245
Leu Arg Lys Arg Tyr Glu Asp Leu Leu Thr Arg Leu Arg Ala Asn Gln
             60                  65                  70 agc tgg gaa gat tcg aac acc gac ctc gtc ccg gcc cct gca gtc cgg    293
Ser Trp Glu Asp Ser Asn Thr Asp Leu Val Pro Ala Pro Ala Val Arg
         75                  80                  85 ata ctc acg cca gaa gtg cgg ctg gga tcc ggc ggc cac ctg cac ctg    341
Ile Leu Thr Pro Glu Val Arg Leu Gly Ser Gly Gly His Leu His Leu
     90                  95                 100 cgt atc tct cgg gcc gcc ctt ccc gag ggg ctc ccc gag gcc tcc cgc    389
Arg Ile Ser Arg Ala Ala Leu Pro Glu Gly Leu Pro Glu Ala Ser Arg
    105                 110                 115 ctt cac cgg gct ctg ttc cgg ctg tcc ccg acg gcg tca agg tcg tgg    437
Leu His Arg Ala Leu Phe Arg Leu Ser Pro Thr Ala Ser Arg Ser Trp
120                 125                 130                 135 gac gtg aca cga ccg ctg cgg cgt cag ctc agc ctt gca aga ccc cag    485
Asp Val Thr Arg Pro Leu Arg Arg Gln Leu Ser Leu Ala Arg Pro Gln
                140                 145                 150 gcg ccc gcg ctg cac ctg cga ctg tcg ccg ccg tcg cag tcg gac       533
Ala Pro Ala Leu His Leu Arg Leu Ser Pro Pro Pro Ser Gln Ser Asp
            155                 160                 165 caa ctg ctg gca gaa tct tcg tcc gca cgg ccc cag ctg gag ttg cac    581
Gln Leu Leu Ala Glu Ser Ser Ser Ala Arg Pro Gln Leu Glu Leu His
        170                 175                 180 ttg cgg ccg caa gcc gcc agg ggg cgc cgc aga gcg cgt gcg cgc aac    629
Leu Arg Pro Gln Ala Ala Arg Gly Arg Arg Ala Arg Ala Arg Asn
    185                 190                 195 ggg gac cac tgt ccg ctc ggg ccc ggg cgt tgc tgc cgt ctg cac acg    677
Gly Asp His Cys Pro Leu Gly Pro Gly Arg Cys Cys Arg Leu His Thr
200                 205                 210                 215 gtc cgc gcg tcg ctg gaa gac ctg ggc tgg gcc gat tgg gtg ctg tcg    725
Val Arg Ala Ser Leu Glu Asp Leu Gly Trp Ala Asp Trp Val Leu Ser
                220                 225                 230 cca cgg gag gtg caa gtg acc atg tgc atc ggc gcg tgc ccg agc cag    773
Pro Arg Glu Val Gln Val Thr Met Cys Ile Gly Ala Cys Pro Ser Gln
            235                 240                 245 ttc cgg gcg gca aac atg cac gcg cag atc aag acg agc ctg cac cgc    821
Phe Arg Ala Ala Asn Met His Ala Gln Ile Lys Thr Ser Leu His Arg
        250                 255                 260 ctg aag ccc gac acg gtg cca gcg ccc tgc tgc gtg ccc gcc agc tac    869
Leu Lys Pro Asp Thr Val Pro Ala Pro Cys Cys Val Pro Ala Ser Tyr
    265                 270                 275 aat ccc atg gtg ctc att caa aag acc gac acc ggg gtg tcg ctc cag    917
Asn Pro Met Val Leu Ile Gln Lys Thr Asp Thr Gly Val Ser Leu Gln
280                 285                 290                 295 acc tat gat gac ttg tta gcc aaa gac tgc cac tgc ata tgagcagtcc     966
Thr Tyr Asp Asp Leu Leu Ala Lys Asp Cys His Cys Ile
                300                 305 tggtccttcc actgtgcacc tgcgcggagg acgcgacctc agttgtcctg ccctgtggaa  1026
tgggctcaag gttcctgaga cacccgattc ctgcccaaac agctgtattt atataagtct  1086
gttatttatt attaatttat tggggtgacc ttcttgggga ctcgggggct ggtctgatgg  1146
aactgtgtat ttatttaaaa ctctggtgat aaaaataaag ctgtctgaac tgttaaaaaa  1206
aaaaaaaaaa aaaa                                                    1220

<210> SEQ ID NO 2
<211> LENGTH: 308
<212> TYPE: PRT
<213> ORGANISM: Homo sapiens
```

-continued

<400> SEQUENCE: 2

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305

<210> SEQ ID NO 3
<211> LENGTH: 31
<212> TYPE: DNA
<213> ORGANISM: Artificial Sequence
<220> FEATURE:
<223> OTHER INFORMATION: Synthetic sequence, secreted iGDPP forward
      primer

<400> SEQUENCE: 3
cgatgacgac aagcttctgt ctctggccga g                              31

<210> SEQ ID NO 4
<211> LENGTH: 33

```
<212> TYPE: DNA
<213> ORGANISM: Artificial Sequence
<220> FEATURE:
<223> OTHER INFORMATION: Synthetic sequence, secreted iGDPP reverse
      primer

<400> SEQUENCE: 4
cagaactttg cagatatcgg cggcttgcgg ccg                              33

<210> SEQ ID NO 5
<211> LENGTH: 33
<212> TYPE: DNA
<213> ORGANISM: Artificial Sequence
<220> FEATURE:
<223> OTHER INFORMATION: Synthetic sequence, secreted dNT37-GDPP forward
      primer

<400> SEQUENCE: 5
cgatgacgac aagcttgcaa gtttcccggg acc                              33

<210> SEQ ID NO 6
<211> LENGTH: 31
<212> TYPE: DNA
<213> ORGANISM: Artificial Sequence
<220> FEATURE:
<223> OTHER INFORMATION: Synthetic sequence, secreted dNT59-GDPP forward
      primer

<400> SEQUENCE: 6
cgatgacgac aagcttcgct acgaggacct g                                31

<210> SEQ ID NO 7
<211> LENGTH: 32
<212> TYPE: DNA
<213> ORGANISM: Artificial Sequence
<220> FEATURE:
<223> OTHER INFORMATION: Synthetic sequence, secreted dNT77-GDPP forward
      primer

<400> SEQUENCE: 7
cgatgacgac aagcttaaca ccgacctcgt cc                               32

<210> SEQ ID NO 8
<211> LENGTH: 31
<212> TYPE: DNA
<213> ORGANISM: Artificial Sequence
<220> FEATURE:
<223> OTHER INFORMATION: Synthetic sequence, secreted dNT94-GDPP forward
      primer

<400> SEQUENCE: 8
cgatgacgac aagcttctgg gatccggcgg c                                31
```

METHODS FOR DETECTING CANCERS, AND DETECTING REAGENT

CROSS REFERENCE TO RELATED APPLICATIONS

This application is a National Stage of International Application No. PCT/JP2018/030916 filed Aug. 22, 2018, claiming priority based on Japanese Patent Application No. 2017-165409 filed Aug. 30, 2017.

INCORPORATION BY REFERENCE OF SEQUENCE LISTING

The content of the electronically submitted sequence listing, file name: Seq_Listing_elec_REVISED.txt; size: 9,429 bytes; and date of creation: Feb. 28, 2020, filed Feb. 28, 2020, is incorporated herein by reference in its entirety.

TECHNICAL FIELD

The present invention relates to a propeptide of Growth and Differentiation Factor 15 (hereinafter also referred to as "GDF15") protein in blood, and a degradation product thereof; as well as a method and a reagent for detecting cancer by measuring the same.

BACKGROUND ART

Tumor markers for detecting cancer generally include those shown in Table 1. However, all of these markers show a low positive rate in initial stages of cancer, and many of the markers have problems, such as, for example, false positivity in benign tumors or inflammations, and inability to detect highly malignant cancer. Therefore, there is a demand for the discovery of a tumor marker capable of detecting these types of cancer in a highly accurate manner, and for the development of a test method using such a marker.

TABLE 1

| Name of diseases | Name of tumor markers | Characteristics |
|---|---|---|
| Pancreatic cancer | CA19-9 | Positive rate in initial stages is not so high |
|  | DUPAN-2 | False positivity in benign tumors |
|  | Span-1 | Low false positivity, with low sensitivity |
|  | Elastase-1 | Shows low values in advanced cancer |
|  | CEA | No organ specificity, with false positivity |
| Colorectal cancer | CEA | No organ specificity, with false positivity |
|  | CA19-9 | Only for late stage cancer |
|  | P53 antibody | No organ specificity, with high positive rate for cancer |
| Breast cancer | CA15-3 | Relatively specific to breast cancer, with low positive rate in initial stages |
|  | CEA | No organ specificity, with false positivity |
|  | NCC-ST-439 | May not be produced in highly malignant cases |
| Lung cancer | CEA | No organ specificity, with false positivity |
| Lung cancer (small cell lung cancer) | proGRP | Relatively high specificity, with low sensitivity |
|  | NSE | Relatively high specificity, with low sensitivity |
| Lung cancer (squamous cell carcinoma) | CYFRA | Relatively high specificity, with low sensitivity |
|  | SCC | Relatively high specificity, with low sensitivity |
| Lung cancer (adenocarcinoma) | SLX | Relatively low false positivity |

Growth and differentiation factor 15 (GDF15) is a protein which is identical to macrophage inhibitory cytokine 1 (MIC-1) and nonsteroidal anti-inflammatory drug-activated gene 1 (NAG-1), and belongs to the TGF-β family. GDF15 is expressed as prepro-GDF15, which contains a secretion signal and a propeptide, and then the secretion signal is cleaved off from the prepro-GDF15 to form pro-GDF15, which is then secreted outside the cell. Pro-GDF15 is stored in the extracellular matrix through the propeptide, and GDF15 forming a dimer is cleaved off from the propeptide by a furin-like protease to be released into blood (Non-patent Document 1). Full-length pro-GDF15 is reported to be fractionated into a molecular weight of about 40,000, and the mature body of GDF15 is reported to be fractionated into a molecular weight of about 15,000 (Non-patent Document 2).

It has been reported that the level of the mature body of GDF15 in blood increases in various types of cancer, such as pancreatic cancer and colorectal cancer, and an increase in the level thereof in blood is found also in diseases other than cancer, such as heart diseases and the like (Patent Documents 1 to 6, Non-patent Documents 3 to 8). In addition, practical applications of GDF15 for controlling appetite and for fetal examination during pregnancy have been attempted (Patent Documents 7 to 8).

However, all of these findings are those regarding the mature body of GDF15, and GDF15 propeptide has been thought to be localized in the extracellular matrix (Non-patent Document 2). Further, the detection of a disease by measuring this protein, and the effects thereof, have not been known.

Note that, GDF15 propeptide (hereinafter also referred to as "GDPP") is a polypeptide of 165 residues located on the N-terminal side of pro-GDF15. More specifically, the GDF15 propeptide in the present specification contains at least an amino acid sequence from the leucine at the 30th residue to the arginine at the 194th residue, which is a sequence following the region of the signal peptide from the initiating methionine to the alanine at the 29th residue, in the amino acid sequence of SEQ ID NO:1 (GenBank Accession No.: NM_004864) based on cDNA of human GDF15, or contains an amino acid sequence having an identity of not less than 80% to the above described sequence.

PRIOR ART DOCUMENTS

Patent Documents

Patent Document 1: JPWO 2011-102461 A1
Patent Document 2: JP 2009-545735 A
Patent Document 3: JP 2010-528275 A
Patent Document 4: JP 2011-523051 A
Patent Document 5: JP 2012-515335 A
Patent Document 6: JPWO 2015-108077 A1
Patent Document 7: JP 2011-190262 A
Patent Document 8: JP 2003-532079 A

Non-Patent Documents

Non-patent Document 1: Prostate Cancer Prostatic Dis. 2012; 15 (4): 320-328
Non-patent Document 2: Cancer Res. 2005; 65 (6): 2330-2336
Non-patent Document 3: Biochemical Pharmacology. 2013; 85:597-606
Non-patent Document 4: Clin Cancer Res. 2009; 15 (21): 6658-6664

Non-patent Document 5: Clin Cancer Res. 2011; 17:4825-4833

Non-patent Document 6: Clin Cancer Res. 2003; 9:2642-2650

Non-patent Document 7: Clin Cancer Res. 2006; 12:442-446

Non-patent Document 8: BMC Cancer. 2014; 14:578-588

SUMMARY OF THE INVENTION

Problems to be Solved by the Invention

An object of the present invention is to provide a method for detecting cancer in a simple and highly accurate manner, and a reagent that can be used in the method.

Means for Solving the Problems

The present inventors have made intensive studies in order to solve the above mentioned problems. As a result, the present inventors have found out that, in an immunoassay using an antibody that recognizes GDF15 propeptide, an increase in the level of GDF15 propeptide in blood is observed in samples of pancreatic cancer, colorectal cancer, lung cancer, breast cancer, esophageal cancer and stomach cancer, as compared to that in healthy samples; and that, in lung cancer, a higher increase in the level of GDF15 propeptide in blood is observed in small cell lung cancer than in non-small cell lung cancer. Based on these findings, the present inventors discovered that GDF15 propeptide can be a potential marker for detecting cancer, particularly, pancreatic cancer, colorectal cancer, lung cancer, breast cancer, esophageal cancer or stomach cancer, or for distinguishing and detecting non-small cell lung cancer and small cell lung cancer in the detection of lung cancer, thereby completing the present invention.

That is, the present invention is as follows.

[1] A method for detecting cancer (excluding castration-resistant prostate cancer), which comprises measuring the intact growth and differentiation factor (GDF15) propeptide level in a sample.

[2] A method for detecting cancer (excluding castration-resistant prostate cancer), which comprises measuring the GDF15 propeptide fragment level in a sample.

[3] A method for detecting cancer (excluding castration-resistant prostate cancer), which comprises measuring the total of the intact GDF15 propeptide level and the GDF15 propeptide fragment level in a sample.

[4] The method for detecting cancer according to any one of [1] to [3], wherein the detected cancer is one or more selected from the group consisting of stomach cancer, pancreatic cancer, colorectal cancer, lung cancer, breast cancer and esophageal cancer, or wherein non-small cell lung cancer and small cell lung cancer are distinguished to be detected.

[5] The method according to [2] or [3], wherein the GDF15 propeptide fragment(s) include(s) the following GDF15 propeptide fragment(s) (A) and/or (B):

(A) a GDF15 propeptide fragment having the following properties:

contains an amino acid sequence from the lysine at the 58th residue to at least the aspartic acid at the 167th residue in the GDF15 amino acid sequence of SEQ ID NO: 2, or a sequence having an identity of not less than 80% thereto;

(B) a GDF15 propeptide fragment having the following properties:

contains an amino acid sequence from the glutamic acid at the 74th residue to at least the aspartic acid at the 167th residue in the GDF15 amino acid sequence of SEQ ID NO: 2, or a sequence having an identity of not less than 80% thereto.

[6] The method according to any one of [1] to [5], wherein the measurement is carried out by an antigen-antibody reaction using an antibody that recognizes GDF15 propeptide.

[7] The method according to any one of [1] to [5], wherein the measurement is carried out using mass spectrometry.

[8] A reagent for detecting cancer (excluding castration-resistant prostate cancer), the reagent including an antibody that recognizes GDF15 propeptide.

Effect of the Invention

The present invention provides a method for detecting cancer in a simple and highly accurate manner, and a reagent that can be used in the method.

The reagent according to the present invention is used for detecting GDF15 propeptide. Since the expression control region of GDF15 is located downstream of p53, it is assumed that GDF15 propeptide level reflects the therapeutic effects of existing cancer therapeutic agents, particularly, taxane-based anticancer drugs. Accordingly, the reagent according to the present invention can also be used as a companion diagnostic agent in the treatment of cancer.

MODE FOR CARRYING OUT THE INVENTION

Figure 1:
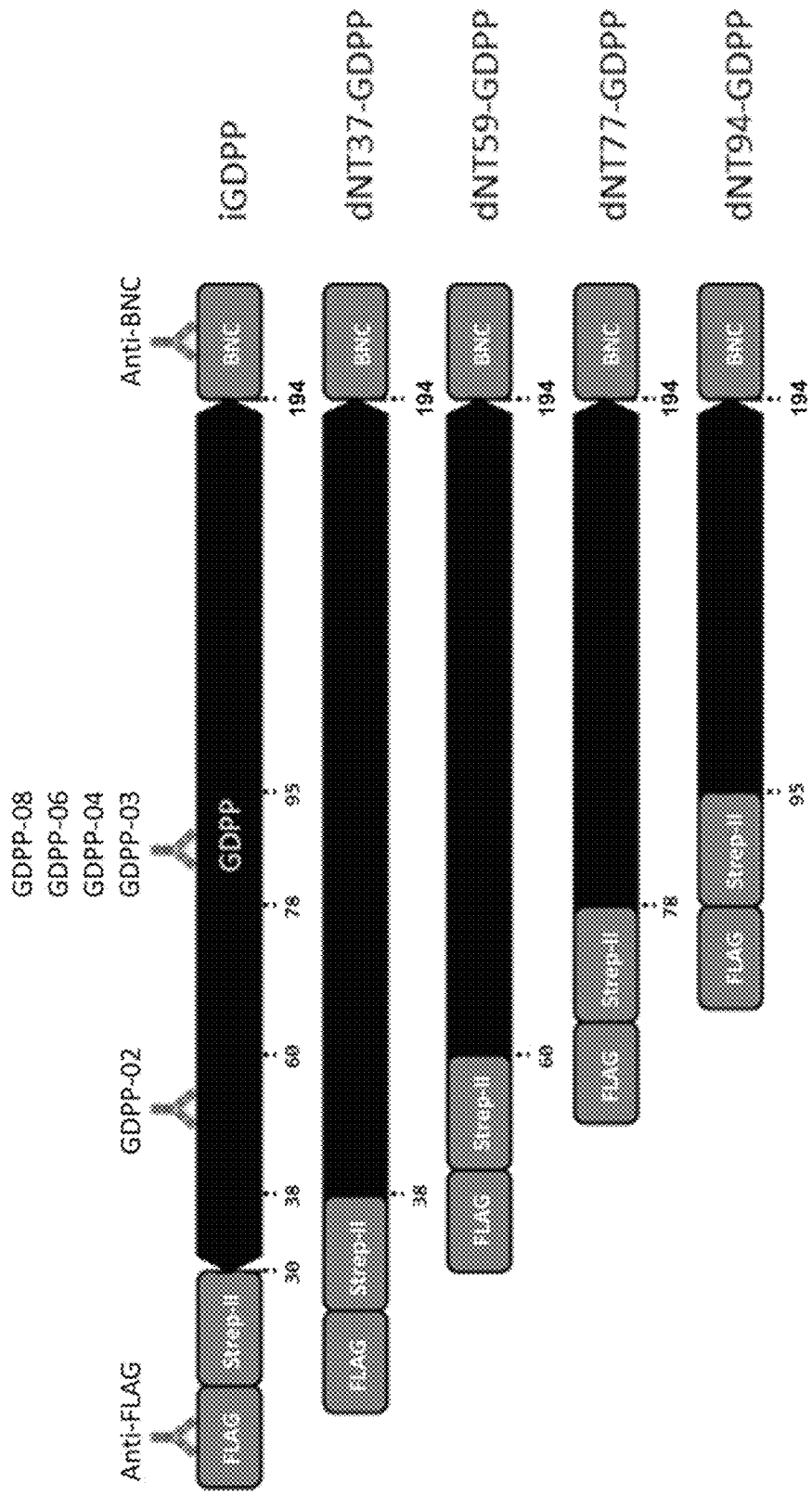
FIG. 1 is a diagram showing the structures of various types of recombinant GDPPs prepared.

<1> Method for Detecting Cancer According to Present Invention

The first aspect of the present invention is a method for detecting cancer (excluding castration-resistant prostate cancer (hereinafter, also referred to as "CRPC")), and the method include measuring the GDF15 propeptide level in a sample. This is a method based on the fact that GDF15 propeptide is characteristically present in a biological sample, such as blood, of an individual with cancer, unlike in a sample of a healthy individual. This method enables, as will be shown in Examples to be described later, to detect cancer (excluding CRPC), for example, in the case of detecting one or more selected from the group consisting of pancreatic cancer, colorectal cancer, lung cancer, breast cancer, esophageal cancer and stomach cancer, or distinguishing and detecting non-small cell lung cancer and small cell lung cancer, with a higher sensitivity and specificity, as compared to the case in which a conventionally known tumor marker (CA19-9 or CEA) is measured.

The GDF15 propeptide to be measured in the present aspect includes intact GDF15 propeptide (hereinafter, also referred to as "iGDPP") which has the amino acid sequence from the leucine at the 30th residue to the arginine at the 194th residue in the GDF15 amino acid sequence of SEQ ID NO:2, and/or GDF15 propeptide fragments. The GDF15 propeptide fragments include dNT57-GDPP (corresponds to a sequence from the 58th residue to the 167th residue of the amino acid sequence of SEQ ID NO:2), dNT73-GDPP (corresponds to a sequence from the 74th residue to the 167th residue of the amino acid sequence of SEQ ID NO:2), and other peptide fragments. Note that, the intact GDF15 propeptide as used herein refers to the GDF15 propeptide that has not been degraded. In the detection method according to the present invention, the method for measuring the GDF15 propeptide level is not particularly limited. Examples of the method include a method utilizing an antigen-antibody reaction using an antibody that recognizes GDF15 propeptide, and a method utilizing mass spectrometry.

Specific examples of the method utilizing an antigen-antibody reaction using an antibody that recognizes GDF15 propeptide include the following.

(a) A competition method in which a labeled measuring object and an antibody that recognizes the measuring object are used, and which utilizes the competitive binding of the labeled measuring object and the measuring object contained in the sample to the antibody.

(b) A method using surface plasmon resonance, in which the sample is brought into contact with a chip on which an antibody that recognizes the measuring object is immobilized, and a signal dependent on the binding of the antibody to the measuring object is detected.

(c) A fluorescence polarization immunoassay in which a fluorescently-labeled antibody that recognizes a measuring object is used, and which utilizes the phenomenon that the binding of the antibody to the measuring object causes an increase in the degree of fluorescence polarization.

(d) A sandwich method in which two types of antibodies (one of which is a labeled antibody) that recognize different epitopes on the measuring object are used, so as to allow the formation of a complex of three molecules, namely, a complex of the two antibodies and the measuring object.

(e) A method in which the measuring object in the sample is concentrated by an antibody that recognizes the measuring object, as a pretreatment, and then the polypeptide in the bound protein is detected using a mass spectrometer or the like.

Although the methods (d) and (e) are simple and highly versatile, the method (d) is more preferred for processing a large number of samples, since the technologies related to the reagents and the devices used in this method have been sufficiently established.

As the antibody that recognizes GDF15 propeptide, an antibody that recognizes the N-terminal region of GDF15 propeptide, for example, an antibody that binds to an antigenic determinant in the region from the leucine at the 30th residue to the arginine at the 57th residue in SEQ ID NO:2 can be preferably used for the measurement of the iGDPP level. Further, an antibody that recognizes the C-terminal region of GDF propeptide, for example, an antibody that binds to an antigenic determinant in the region from the glutamic acid at the 74th residue to the arginine at the 194th residue in SEQ ID NO:2 can be preferably used for the measurement of the total of the iGDPP level and the GDPP fragment level (total GDPP; hereinafter also referred to as "tGDPP").

The antibody that recognizes GDF15 propeptide can be obtained by immunizing an animal using as an immunogen, for example, GDF15 propeptide itself, an oligopeptide composed of a partial region of GDF15 propeptide, or a polynucleotide encoding intact pro-GDF15 protein or a partial region thereof.

The animal to be used for the immunization is not particularly limited as long as the animal has ability to produce antibodies. The animal may be a mammal normally used for immunization, such as mouse, rat or rabbit, or may be a bird such as chicken.

Note that, in cases where GDF15 propeptide itself or an oligopeptide composed of a partial region of GDF15 propeptide is used as the immunogen, the structure of the protein or the oligopeptide may change during the preparation process thereof. Therefore, the resulting antibody may not have a high specificity or binding capacity to the desired antigen, in some cases, possibly resulting in a failure to accurately quantify the level of GDF15 propeptide contained in the sample. On the other hand, in cases where an expression vector containing a polynucleotide encoding intact pro-GDF15 protein or a partial region thereof is used as the immunogen, the intact GDF15 propeptide protein or the partial region thereof introduced is expressed as it is, without undergoing a structural change in the body of the immunized animal. Therefore, an antibody having a high specificity and binding capacity (namely, a high affinity) to the GDF15 propeptide in the sample can be obtained, which is preferred.

The antibody that recognizes GDF15 propeptide may be either a monoclonal antibody or a polyclonal antibody. The antibody is preferably a monoclonal antibody.

The establishment of a hybridoma cell that produces an antibody that recognizes GDF15 propeptide can be carried out by a method selected as appropriate from methods whose techniques have been established. For example, a hybridoma cell that produces a monoclonal antibody that recognizes GDF15 propeptide can be established by collecting B cells from an animal immunized by the above method, fusing the B cells with myeloma cells electrically or in the presence of polyethylene glycol, selecting a hybridoma cell that produces a desired antibody using HAT medium, and preparing the selected hybridoma cell into a monoclone by the limiting dilution method.

The selection of the antibody that recognizes GDF15 propeptide, for example, the monoclonal antibody that recognizes GDF15 propeptide, to be used in the method for detecting cancer according to the present invention, can be carried out based on affinity to a GPI (glycosyl phosphatidyl inositol)-anchor type GDF15 propeptide or secretory GDF15 propeptide derived from a host expression system.

Note that, the host is not particularly limited, and can be selected as appropriate from cells of microorganisms such as E. coli and yeast, insect cells and animal cells that are usually used for protein expression by those skilled in the art. The host is preferably a mammalian cell, since it enables the expression of a protein having a structure similar to that of natural GDF15 propeptide by post-translational modification such as disulfide bonding or glycosylation. Examples of the mammalian cell include the human embryonic kidney (HEK)-derived 293T cell line, monkey kidney COST cell line, Chinese hamster ovary (CHO) cells, and cancer cells isolated from humans, which are conventionally used.

The purification of the antibody to be used in the method for detecting cancer according to the present invention can be carried out by a method selected as appropriate from methods whose techniques have been established. For example, after culturing hybridoma cells which are established by the above method and which produce an antibody, the culture supernatant may be collected, and the antibody may be concentrated, if necessary, by ammonium sulfate precipitation. Thereafter, affinity chromatography using a carrier to which Protein A, Protein G, Protein L or the like is immobilized, and/or ion-exchange chromatography can be carried out to achieve the purification of the antibody.

Note that, the labeled antibody to be used for the antigen-antibody reaction in the sandwich method described above can be prepared by labeling an antibody purified by the above method with, for example, an enzyme such as peroxidase or alkaline phosphatase. The labeling may also be carried out using a method whose technique has been sufficiently established.

The method for detecting GDF15 propeptide utilizing mass spectrometry, in the detection method according to the present invention, will be specifically described below.

In the case of using blood as a sample, it is preferred that proteins such as albumin, immunoglobulin and transferrin, which are contained in large amounts in blood, be removed as a pretreatment step, using Agilent Human 14 or the like, followed by further fractionation by ion exchange, gel filtration, reverse-phase HPLC, and/or the like.

The measurement can be carried out by tandem mass spectrometry (MS/MS), liquid chromatography-tandem mass spectrometry (LC/MS/MS), matrix assisted laser desorption ionization time-of-flight mass spectrometry (MALDI-TOF/MS), surface enhanced laser desorption ionization mass spectrometry (SELDI-MS), or the like.

In the detection method according to the present invention, it is preferred to determine that pancreatic cancer, colorectal cancer, lung cancer, breast cancer, stomach cancer or esophageal cancer is detected, when the GDF15 propeptide level obtained by the measurement is higher than a reference value (cutoff value) calculated from a control. Further, in the method for distinguishing and detecting non-small cell lung cancer and small cell lung cancer, according to the present invention, it is preferred to determine that small cell lung cancer is detected when the GDF15 propeptide level is higher than a reference value (cutoff value) calculated from non-small cell lung cancer.

The GDF15 propeptide level to be used for the determination may be either a measured value or a converted concentration value. Note that, the converted concentration value refers to a value converted from a measured value based on a calibration curve prepared using GDF15 propeptide as a standard sample. The concentration of the standard sample may be determined as a value converted from a measured value based on a calibration curve of a standard peptide, prepared using mass spectrometry.

The reference value (cutoff value) may be set as appropriate to a measured value which provides an optimum sensitivity and specificity, by measuring samples of healthy individuals and samples of pancreatic cancer, colorectal cancer, lung cancer, breast cancer, esophageal cancer or stomach cancer, or alternatively, by measuring samples of non-small cell lung cancer and samples of small cell lung cancer, and then carrying out the receiver operating characteristic (ROC) curve analysis.

<2> Reagent for Detecting Cancer according to Present Invention

The second aspect of the present invention is a reagent for detecting one or more selected from pancreatic cancer, colorectal cancer, lung cancer, breast cancer, esophageal cancer and stomach cancer, or distinguishing and detecting non-small cell lung cancer and small cell lung cancer, and the reagent contains an antibody that recognizes GDF15 propeptide. The antibody is usually an antibody that binds to an antigenic determinant in the region from the leucine at the 30th residue to the arginine at the 194th residue in the pro-GDF15 represented by SEQ ID NO:2.

The GDF15 propeptide to be detected in the present aspect includes intact GDF15 propeptide and/or GDF15 propeptide fragments. The GDF15 propeptide fragments include dNT57-GDPP, dNT73-GDPP, and other peptide fragments.

In cases where the reagent according to the present invention is used in the sandwich method described above, the reagent needs to contain, as the antibody, two types of antibodies specific for different epitopes.

The detection reagent according to the present invention may further contain a detection reagent for detecting a cancer tumor marker, which detection reagent contains an antibody that recognizes the cancer tumor marker. Examples of the cancer tumor marker include those shown in Table 1.

The antibody contained in the reagent according to the present invention may be an antibody itself, a labeled antibody, or an antibody immobilized on a solid phase.

The reagent according to the present invention will now be specifically described, regarding the case in which the reagent is used in a two-step sandwich method, which is one embodiment of the sandwich method described above. However, the present invention is not limited thereto.

The reagent according to the present invention can be prepared by the method described in the following (I) to (I11).

(I) Of the two types of antibodies (hereinafter referred to as "Antibody 1" and "Antibody 2") that recognize different epitopes on GDF15 propeptide and that are used in the sandwich method, Antibody 1 is first bound to a carrier capable of B/F (Bound/Free) separation, such as an immunoplate or magnetic particles. The Antibody 1 may be physically bound to the carrier utilizing hydrophobic bonding, or may be chemically bound thereto using, for example, a linker reagent capable of cross-linking two substances to each other.

(II) After binding the Antibody 1 to the carrier, the surface of the carrier is subjected to a blocking treatment using bovine serum albumin, skim milk, a commercially available immunoassay blocking agent or the like, for preventing non-specific binding, to provide a primary reagent.

(III) The other antibody, Antibody 2, is then labeled, and a solution containing the resulting labeled antibody is prepared as a secondary reagent. Preferred examples of the substance to be used for labeling the Antibody 2 include enzymes such as peroxidase and alkaline phosphatase; substances detectable by detection devices, such as fluorescent substances, chemiluminescent substances and radioisotopes; and substances to which another molecule specifically binds, such as biotin, to which avidin specifically binds. Preferred examples of the solution to be used for the secondary reagent include buffers which allow an antigen-antibody reaction to proceed favorably, such as phosphate buffer and Tris-HCl buffer.

The thus prepared reagent according to the present invention may be freeze-dried, if necessary.

Note that, in the case of performing a one-step sandwich method, the binding of Antibody 1 to the carrier and subsequent blocking treatment can be carried out in the same manner as in (I) and (II) to prepare an antibody-immobilized carrier, and a buffer containing a labeled Antibody 2 can be further added to the antibody-immobilized carrier, to prepare a reagent.

For the detection and measurement of GDF15 propeptide by a two-step sandwich method, using the reagent obtained by the method described above, the method described in the following (IV) to (VI) can be carried out.

(IV) The primary reagent prepared in (II) is brought into contact with a sample for a predetermined period of time at a constant temperature. The reaction can be carried out under the conditions of a temperature within the range of from 4° C. to 40° C. for 5 minutes to 180 minutes.

(V) Unreacted substances are removed by B/F separation, and then the secondary reagent prepared in (III) is brought into contact with the reaction product for a predetermined period of time at a constant temperature, to allow the formation of a sandwich complex. The reaction can be carried out under the conditions of a temperature within the range of from 4° C. to 40° C. for 5 minutes to 180 minutes.

(VI) Unreacted substances are removed by B/F separation, and the labeling substance of the labeled antibody is quantified. Based on a calibration curve prepared using a GDF15 propeptide solution having a known concentration as a standard, the concentration of human GDF15 propeptide in the sample is quantified.

The amount of each reagent component, such as the antibody contained in the detection agent, can be set as appropriate depending on the conditions such as the amount of the sample, the type of the sample, the type of the reagent, and the detection method. Specifically, for example, in cases where the GDF15 propeptide level is measured as described below by a sandwich method using 50 µL of 2.5-fold diluted serum or plasma as a sample, the amount of the antibody to be bound to the carrier may be from 100 ng to 1,000 µg, and the amount of the labeled antibody may be from 2 ng to 20 µg in a reaction system in which 50 µL of the sample is reacted with the antibodies.

The reagent for detecting cancer according to the present invention is applicable to either manual detection or detection using an automatic immunodiagnostic apparatus. In particular, the detection using an automatic immunodiagnostic apparatus is preferred, since it enables the detection of cancer without being affected by endogenous measurement-interference factors and competing enzymes contained in the sample, and also enables the quantification of the concentrations of GDF15 propeptide and a cancer tumor marker in the sample, in a short period of time.

Examples of the sample (test sample) to be measured by the method for detecting cancer according to the present invention and the detection reagent according to the present invention include: blood components such as whole blood, blood cells, serum and plasma; extracts from cells and tissues; urine; and cerebrospinal fluid. The body fluids such as blood components or urine is preferably used as the sample, since it allows for detecting cancer in a simple and noninvasive manner. From the viewpoint of the ease of sample collection and versatility for other test items, the use of a blood component as the sample is particularly preferred. The dilution rate of the sample may be selected as appropriate from no dilution to 100-fold dilution depending on the type and the conditions of the sample used. In the case of serum or plasma, for example, 50 µL of a 2.5-fold diluted sample can be used.

EXAMPLES

Examples will be shown below for specifically describing the present invention. The following Examples are provided for illustrating the present invention, and the present invention is in no way limited to these Examples.

<Example 1> Preparation of Monoclonal Antibodies

Five types of monoclonal antibodies that recognize GDF15 propeptide were prepared by a known method (DNA immunization, JP 2013-061321 A).

<Example 2> Epitope Analysis of Monoclonal Antibodies

The antigen recognition site of each type of antibody prepared in Example 1 was identified using culture supernatants of cells expressing intact GDF15 propeptide (iGDPP) and N-terminal deletion variants of the GDF15 propeptide fragment (dNT-GDPP).

For the expression evaluation and the purification process of each recombinant GDPP, a FLAG tag and a Strep II tag were inserted into the 5'-end, and an oligonucleotide encoding BNC peptide (JP 2009-240300 A), which is composed of the seven amino acids on the C-terminal side of BNP (brain natriuretic peptide), was inserted into the 3'-end, to prepare plasmids capable of expressing secretory iGDPP and four types of dNT-GDPPs. FIG. 1 shows the structures of various types of recombinant GDPPs prepared, and specific detail of the preparation method will be described below.

Note that, as shown in FIG. 1, in the amino acid sequence of SEQ ID NO:2, iGDPP corresponds to a sequence from the 30th residue to the 194th residue, dNT37-GDPP corresponds to a sequence from the 38th residue to the 194th residue, dNT59-GDPP corresponds to a sequence from the 60th residue to the 194th residue, dNT77-GDPP corresponds to a sequence from the 78th residue to the 194th residue, and dNT94-GDPP corresponds to a sequence from the 95th residue to 194th residue.

(1) Using primers designed based on cDNA of human GDF15 (GenBank Accession No.: NM 004864) in the combinations shown in Table 2, polynucleotides corresponding to iGDPP, dNT37-GDPP, dNT59-GDPP, dNT77GDPP and dNT94-GDPP were amplified by RT-PCR according to a conventional method.

TABLE 2

| Recombinant GDPP | Forward primer | Reverse primer |
|---|---|---|
| Secretory iGDPP | SEQ ID NO: 3: The 15 bases on the 3'-end correspond to the base sequence of positions 120 to 134 in SEQ ID NO: 1 | SEQ ID NO: 4: The 15 bases on the 5'-end correspond to the base sequence of positions 585 to 599 in SEQ ID NO: 1 |

TABLE 2-continued

| Recombinant GDPP | Forward primer | Reverse primer |
|---|---|---|
| Secretory dNT37-GDPP | SEQ ID NO: 5: The 17 bases on the 3'-end correspond to the base sequence of positions 144 to 160 in SEQ ID NO: 1 | |
| Secretory dNT59-GDPP | SEQ ID NO: 6: The 15 bases on the 3'-end correspond to the base sequence of positions 207 to 221 in SEQ ID NO: 1 | |
| Secretory dNT77-GDPP | SEQ ID NO: 7: The 16 bases on the 3'-end correspond to the base sequence of positions 261 to 276 in SEQ ID NO: 1 | |
| Secretory dNT94-GDPP | SEQ ID NO: 8: The 15 bases on the 3'-end correspond to the base sequence of positions 115 to 229 in SEQ ID NO: 1 | |

(2) Each RT-PCR amplification product prepared in (1) was inserted into the HindIII-EcoRI site of pFLAG1 (manufactured by SIGMA), which is a plasmid containing the GPI anchor region of placental alkaline phosphatase, using In-fusion (manufactured by Clontech) according to the product protocol, to construct each secretory-GDPP expression plasmid.

(3) In order to confirm that each secretory GDPP expressed from each polynucleotide inserted into the plasmid pFLAG1 has the FLAG tag on the N-terminal side and the BNC tag on the C-terminal side, a test was carried out by the following method using the cell line of 293T cells, which are transiently expressing cells.

(4) Each secretory GDPP expression plasmid constructed in (2) was introduced into the 293T cell line according to a conventional method, and each secretory GDPP was transiently expressed. After culturing for 72 hours, the culture liquid was centrifuged, and the resulting supernatant was collected as each secretory GDPP solution.

(5) Using each secretory GDPP solution as a sample, an enzyme immunoassay (ELISA) was carried out as follows.
(5-1) A rabbit anti-FLAG polyclonal antibody (manufactured by ROCKLAND) was diluted with a carbonate buffer (pH 9.8) to a concentration of 100 ng/well, and then immobilized on a MaxiSorp 96-well plate (manufactured by NUNC).
(5-2) After allowing the reaction to proceed at 4° C. overnight, the plate was washed three times with TBS (Tris-Buffered Saline), and a TBS solution supplemented with 3% bovine serum albumin (BSA) was added to each well at 250 µL/well. The plate was then left to stand at room temperature for two hours.
(5-3) The plate was then washed three times with TBS. Each secretory GDPP solution and, as a negative control, the culture supernatant of the 293T cell line to which no expression plasmid was introduced were added to the plate at 50 µL/well. The plate was then left to stand at room temperature for one hour.
(5-4) After washing the plate three times with TBS supplemented with 0.5% Tween 20 (TBS-T), a mouse anti-BNC monoclonal antibody solution diluted to 1 µg/mL with TBS-T supplemented with 1% BSA (1% BSA/TBS-T), or each monoclonal antibody, was added to the plate at 50 µL/well. The plate was then left to stand at room temperature for one hour.

Figure 2:
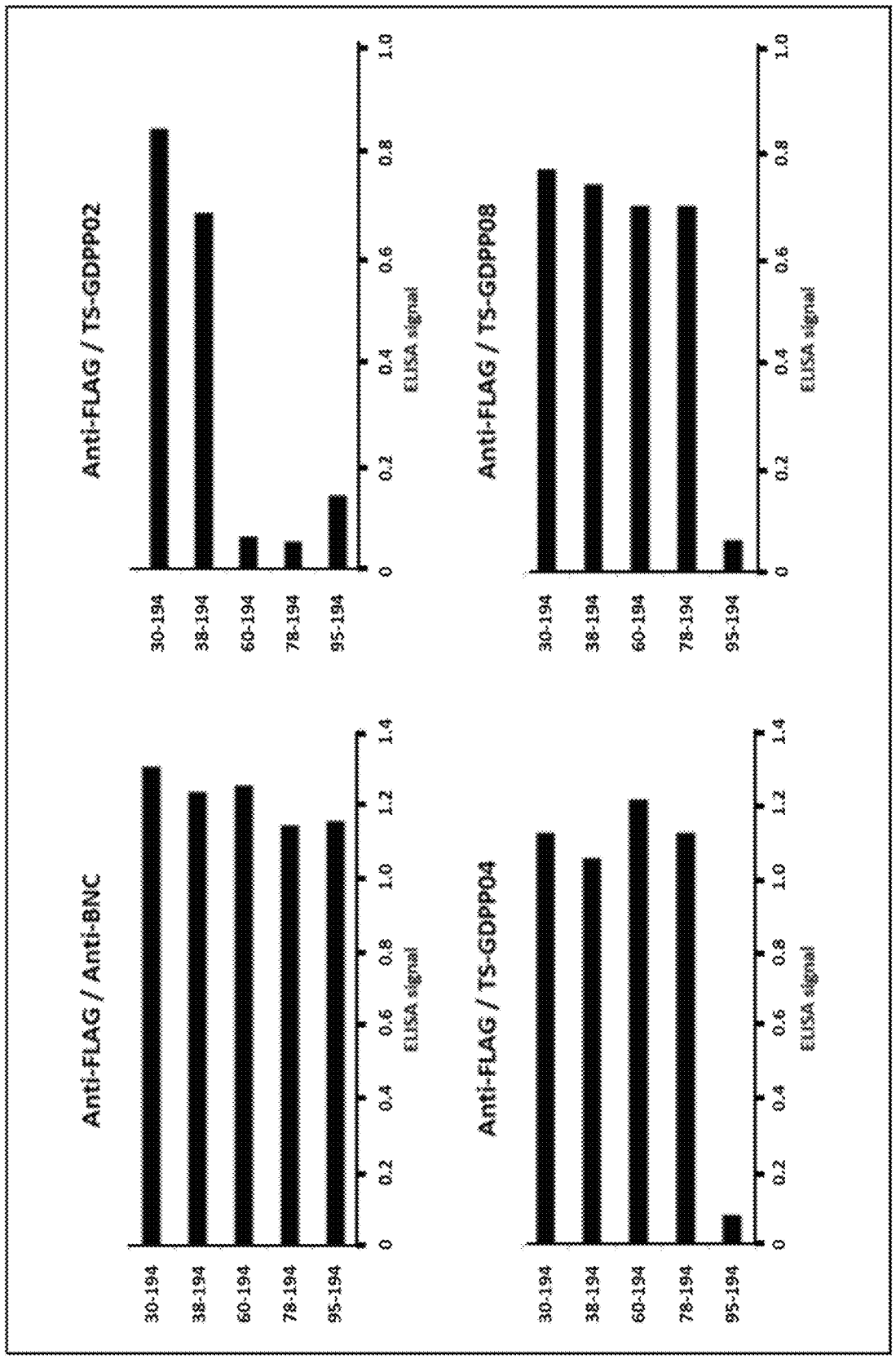
FIG. 2 is a diagram showing the results of ELISA analysis.

(5-5) After washing the plate three times with TBS-T, a horseradish peroxidase (HRP)-labeled anti-mouse immunoglobulin G-Fc antibody (manufactured by SIGMA) solution diluted 10,000-fold with 1% BSA/TBS-T was added to the plate at µL/well. The plate was then left to stand at room temperature for one hour.
(5-6) After washing the plate four times with TBS-T, TMB Microwell Peroxidase Substrate (manufactured by KPL) was added to the plate, and the reaction was stopped with a 1 mol/L phosphoric acid solution, followed by measuring the absorbance at 450 nm using an absorbance plate reader.
(5-7) The results of the ELISA analysis are shown in FIG. 2, and the antigen recognition sites of the respective antibodies are shown in Table 3.

TABLE 3

| Antibody No. | Antigen recognition site |
|---|---|
| TS-GDPP02 | $38^{th}$-$58^{th}$ amino acid residue |
| TS-GDPP03 | $78^{th}$-$95^{th}$ amino acid residue |
| TS-GDPP04 | |
| TS-GDPP06 | |
| TS-GDPP08 | |

<Example 3> Preparation of GDF15 Propeptide Assay Reagents

Using the anti-GDPP monoclonal antibodies prepared in Example 1, two types of GDPP assay reagents were prepared with different combinations of the antibodies. One of the reagents is based on the combination of an antibody (TS-GDPP02) that recognizes the N-terminal region of GDPP and an antibody (TS-GDPP04) that recognizes the C-terminal region of GDPP, and this reagent detects intact GDPP (iGDPP). The other reagent is based on the combination of antibodies (TS-GDPP04 and TS-GDPP08) each of which recognizes the C-terminal region of GDPP, and this reagent detects both iGDPP and dNT-GDPPs. The value detected by the latter reagent is defined as the total GDPP (tGDPP). The preparation method thereof will be described below in specific detail.

(1) An anti-GDF15 propeptide monoclonal antibody (TS-GDPP 02 or 08) was physically adsorbed to water insoluble ferrite carriers for a whole day and night at room temperature to an adsorption amount of 100 ng/carrier, followed by blocking with a 100 mM tris buffer (pH 8.0) supplemented with 1% BSA at 40° C. for four hours, to prepare each type of anti-GDF15 propeptide antibody-immobilized carriers.
(2) An anti-GDF15 propeptide monoclonal antibody (TS-GDPP04) was labeled using an alkaline phosphatase labeling kit (manufactured by Dojindo Laboratories), to prepare a labeled anti-GDF15 propeptide antibody.
(3) Twelve pieces of each type of the antibody immobilized carriers prepared in (1) were introduced into an individual magnetic permeable container (having a capacity of 1.2 mL). Thereafter, 50 µL of a buffer (tris buffer supplemented with 3% BSA, pH 8.0) containing 0.5 µg/mL of the labeled antibody prepared in (2) was added to each container, followed by freeze drying, to prepare each type of GDF15 propeptide assay reagent. Note that, the thus prepared GDF15 propeptide assay reagents were tightly closed and sealed under nitrogen gas, and stored at 4° C. until the assay.

<Example 4> Preparation of GDF15 Propeptide Standard Product

Since degradation products are present in the secretory type iGDPP culture supernatant prepared in Example 2, full-length GDF15 propeptide alone was purified using a commercially available purification kit (manufactured by IBA), utilizing the Strep-II tag (manufactured by IBA) located on the N-terminal side of the recombinant iGDPP. The secretory type iGDPP after the purification was evaluated by Western blotting. Various purified samples were developed by SDS-PAGE according to a conventional method, and transferred to a PVDF membrane (manufactured by Bio-Rad Laboratories). The membrane was blocked with Blocking One solution (manufactured by Nacalai Tesque), and then an alkaline phosphatase-labeled anti-BNC antibody was added to the blocking solution at 1 µg/sheet, followed by allowing the reaction to proceed at 4° C. overnight. After washing the membrane with TBS-T, ECL Select Reagent (manufactured by GE Healthcare) was used, and the resulting chemiluminescence was detected using a LAS 4000 image analyzer (manufactured by GE Healthcare).

Figure 3:
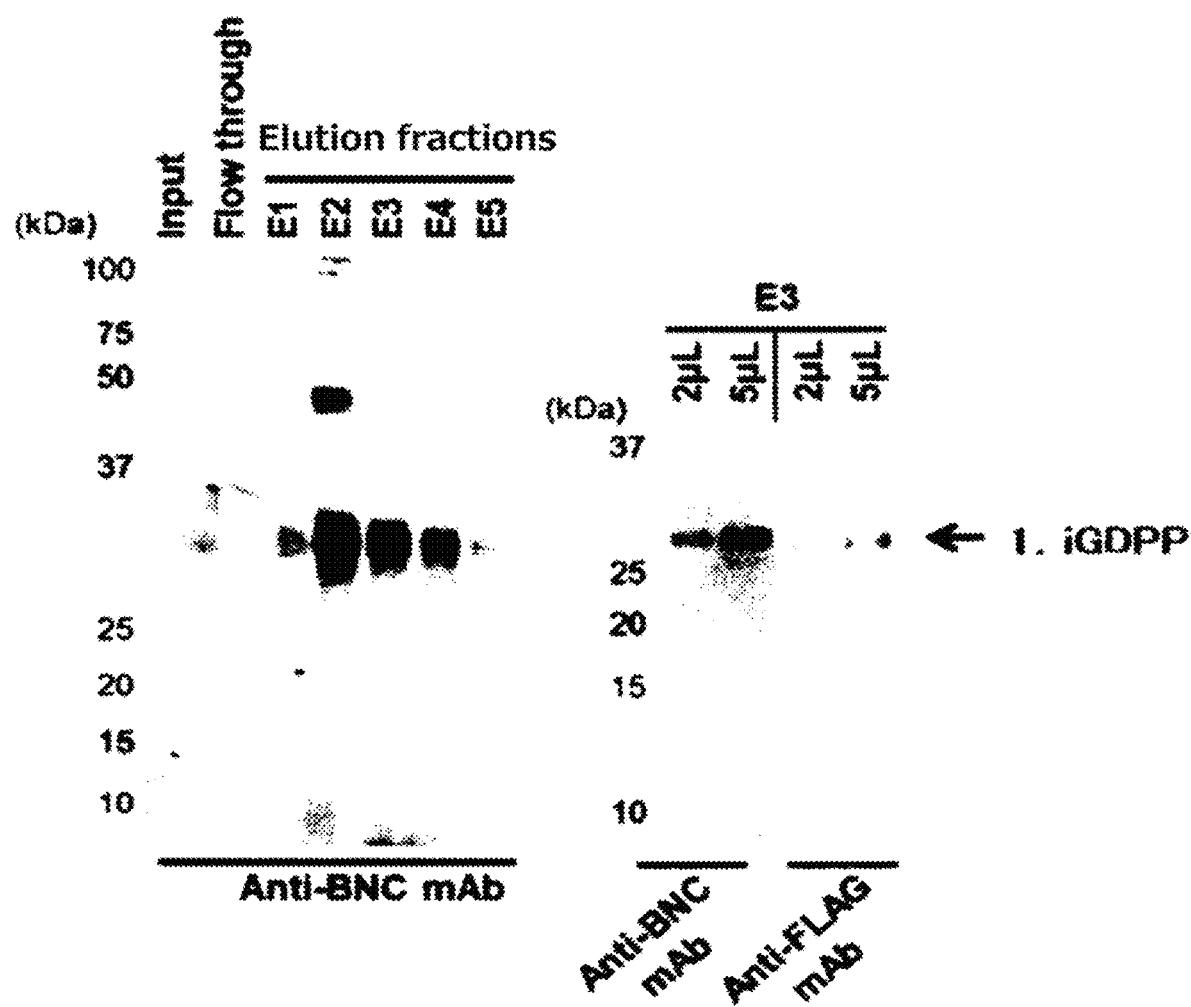
FIG. 3 is a diagram showing the results of Western blotting.

The results of the Western blotting of the purified GDPP product are shown in FIG. 3. Although an increase in the molecular weight was observed due to the addition of the tag peptides, a single band corresponding to the full-length GDF15 propeptide was detected by using either an N-terminal tag antibody or a C-terminal tag antibody.

<Example 5> Performance Evaluation of GDF15 Propeptide Assay Reagents

The recombinant GDPP supernatant prepared in Example 4 and the culture supernatant of the prostate cancer cell line LnCap were each diluted 10-fold with FBS, to be used as samples containing GDF15 propeptide, and a sample of FBS alone was prepared as a sample which does not contain GDF15 propeptide, to give a total of three types of pseudosamples. A fully automatic enzyme immunoassay apparatus, AIA-2000 (manufactured by Tosoh Corporation, manufacturing/marketing notification number: 13B3X90002000009), was used to evaluate the performance of the two types of GDF15 propeptide assay reagents prepared in Example 3. The measurement using the fully automatic enzyme immunoassay apparatus, AIA-2000, was carried out by:
 (1) automatically dispensing 20 µL of a diluted sample and 80 µL of a diluent containing a surfactant into a container containing a GDF15 propeptide assay reagent prepared in Example 3;
 (2) allowing an antigen-antibody reaction to proceed at a constant temperature of 37° C. for ten minutes;
 (3) carrying out washing eight times, with a buffer containing a surfactant; and (4) adding 4-methylumbelliferyl phosphate.
The concentration of 4-methylumbelliferone produced by alkaline phosphatase per unit time was taken as the measured value (nmol/(Ls)). As a result of the AIA measurement, each of the pseudosamples excluding FBS showed a coefficient of variation of not more than 3% in the five-point measurement. It has thus been demonstrated that the results obtained using the GDF15 propeptide assay reagents prepared in Example 3 are reliable.

<Example 6> Measurement of Clinical Samples

The details of the serum sample panel (total of 123 cases) used in the present Example are shown in Table 4. The serum samples of healthy individuals were purchased from BioreclamationIVT, and various cancer serum samples were purchased from PROMEDDX. It is clearly described in the documents attached to the products of both companies, that these samples were collected in accordance with the protocols approved by the ethics committee.

TABLE 4

|  | | Male | | Female | |
| --- | --- | --- | --- | --- | --- |
|  | Number of samples | Number of samples | Age | Number of samples | Age |
| Healthy individuals | 60 | 30 | 62 ± 3.0 | 30 | 62 ± 1.6 |
| Lung cancer | 18 | 7 | 69 ± 3.2 | 11 | 69 ± 8.2 |
| Breast cancer | 11 | 0 | — | 11 | 68 ± 5.4 |
| Pancreatic cancer | 18 | 6 | 69 ± 9.0 | 12 | 71 ± 9.9 |
| Colorectal cancer | 16 | 6 | 65 ± 9.0 | 10 | 61 ± 7.9 |
| Total number of samples | 123 | | | | |

Figure 4:
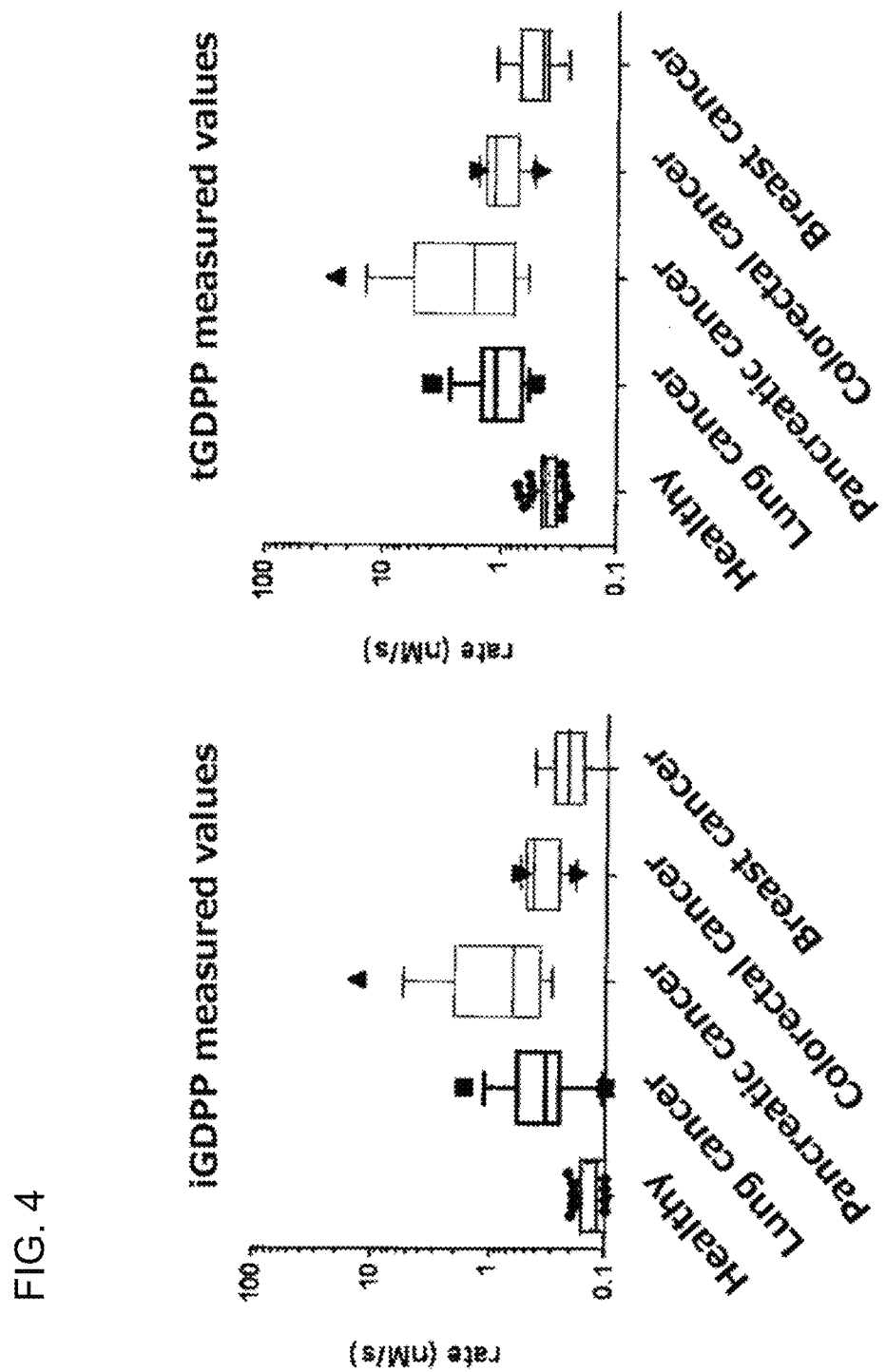
FIG. 4 is a diagram showing box plots of various measured values.

Using a fully automatic enzyme immunoassay apparatus AIA-2000 (manufactured by Tosoh Corporation) as an apparatus for the evaluation, the clinical samples were measured using the iGDPP and tGDPP assay reagents prepared in Example 3. The box plots of various measured values are shown in FIG. 4, and the minimum value, the 25 percentile, the median value, the 75 percentile, the maximum value, and the range of measured values in the 95% confidence interval, of the measured values of iGDPP and tGDPP in each of the sample groups, are shown in Table 5. The measured values of iGDPP and tGDPP were clearly higher in all of the cancer groups, as compared to the healthy group. In particular, a tendency for higher measured values was observed in pancreatic cancer and colorectal cancer, which are major types of gastrointestinal cancer.

TABLE 5

|  | Healthy individuals | Lung cancer | Pancreatic cancer | Colorectal cancer | Breast cancer |
| --- | --- | --- | --- | --- | --- |
| iGDPP measured values | | | | | |
| Minimum value | 0.07 | 0.10 | 0.30 | 0.18 | 0.09 |
| 25 percentile | 0.09 | 0.26 | 0.38 | 0.27 | 0.16 |
| Median value | 0.12 | 0.33 | 0.65 | 0.44 | 0.22 |
| 75 percentile | 0.16 | 0.57 | 2.00 | 0.51 | 0.29 |
| Maximum value | 0.21 | 1.66 | 13.50 | 0.56 | 0.43 |
| 95% confidence interval | 0.12-0.14 | 0.28-0.66 | 0.35-3.54 | 0.32-0.46 | 0.17-0.29 |
| tGDPP measured values | | | | | |
| Minimum value | 0.26 | 0.51 | 0.60 | 0.47 | 0.27 |
| 25 percentile | 0.34 | 0.66 | 0.80 | 0.73 | 0.41 |
| Median value | 0.40 | 1.11 | 1.75 | 1.16 | 0.45 |
| 75 percentile | 0.45 | 1.48 | 5.68 | 1.38 | 0.72 |
| Maximum value | 0.72 | 3.95 | 26.10 | 1.64 | 1.12 |
| 95% confidence interval | 0.39-0.44 | 0.85-1.70 | 1.39-7.88 | 0.88-1.28 | 0.40-0.74 |

Figure 5:
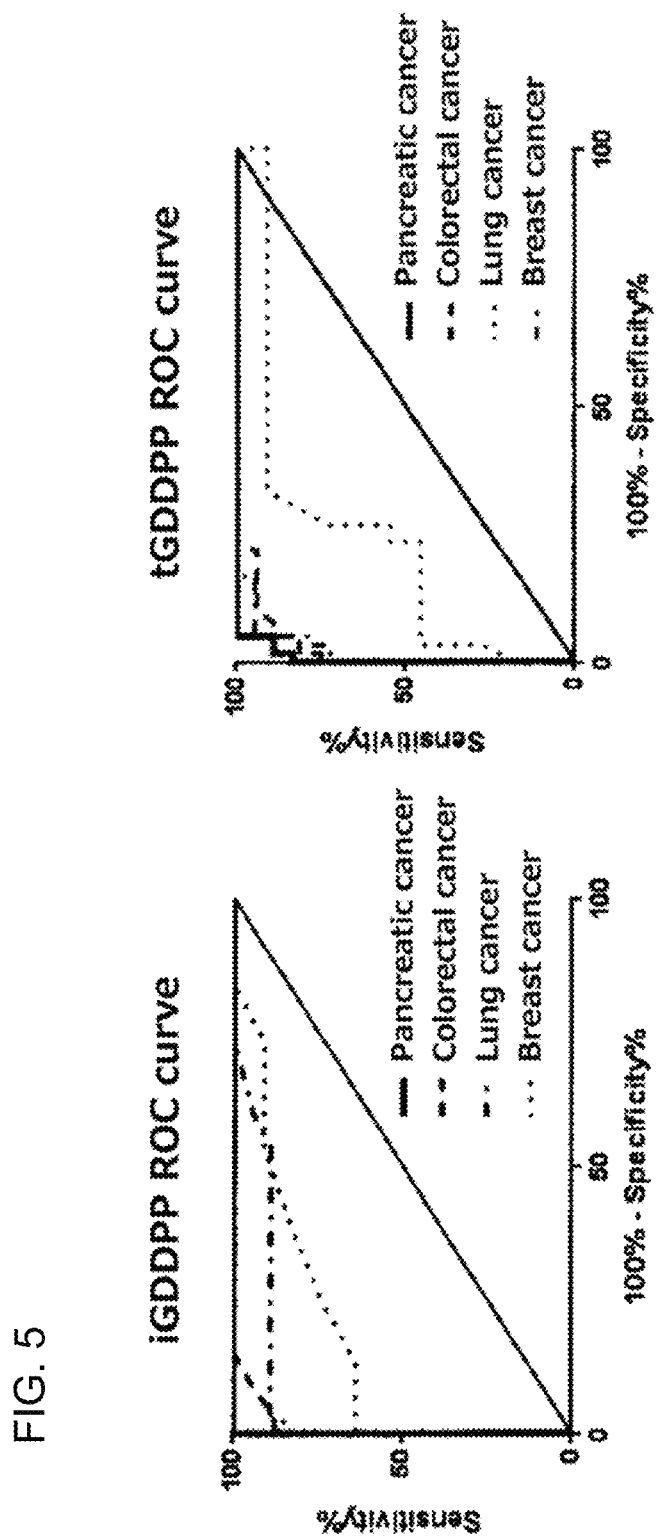
FIG. 5 is a diagram showing the results of receiver operating characteristic (ROC) curve analysis.

The results of the receiver operating characteristic (ROC) curve analysis of iGDPP and tGDPP between the group of healthy individuals and each of the cancer sample groups are shown in FIG. 5, and the values of AUC (Area Under the Curve; the area under the ROC curve), and the P values in the significance test are shown in Table 6. A statistically significant difference was observed between the healthy individuals and each of all the cancer types, revealing an excellent cancer detection performance of iGDPP and tGDPP. In particular, the values of AUC were 0.9 or greater in lung cancer, pancreatic cancer and colorectal cancer, and it has been shown that iGDPP and tGDPP are extremely useful in distinguishing cancer samples from healthy samples.

TABLE 6

|  | Lung cancer | | Pancreatic cancer | | Colorectal cancer | | Breast cancer | |
| --- | --- | --- | --- | --- | --- | --- | --- | --- |
|  | iGDPP | tGDPP | iGDPP | tGDPP | iGDPP | tGDPP | iGDPP | tGDPP |
| AUC | 0.93 | 0.98 | 1.00 | 0.99 | 0.99 | 0.98 | 0.84 | 0.78 |
| Standard error | 0.05 | 0.01 | 0.00 | 0.01 | 0.01 | 0.02 | 0.08 | 0.09 |
| 95% confidence interval | 0.84 to 1.02 | 0.96 to 1.01 | 1.00 to 1.00 | 0.98 to 1.01 | 0.97 to 1.01 | 0.94 to 1.01 | 0.69 to 1.00 | 0.60 to 0.96 |
| P value | <0.0001 | <0.0001 | <0.0001 | <0.0001 | <0.0001 | <0.0001 | <0.0008 | <0.0071 |

<Example 7> Performance Comparison with CA19-9

Figure 6:
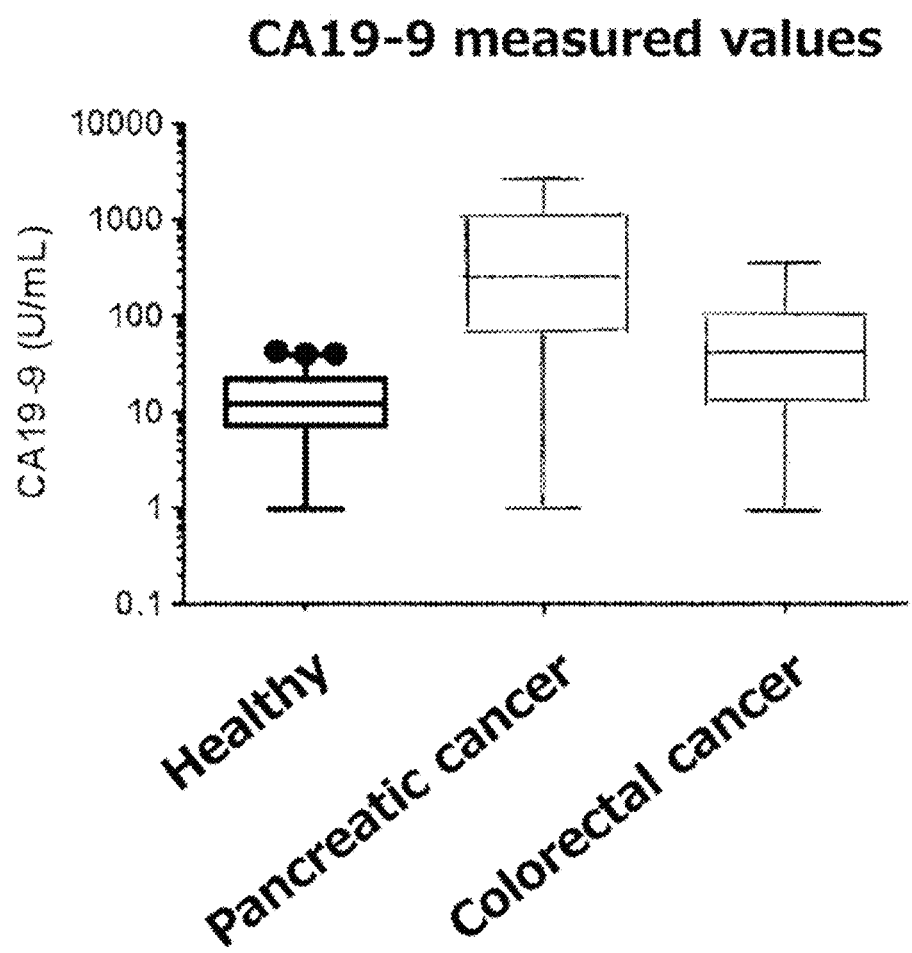
FIG. 6 is a diagram showing the results of the measurement and analysis carried out in Example 6.

The performance of iGDPP and tGDPP for detecting gastrointestinal cancer was compared with that of CA19-9, which is a representative marker for detecting gastrointestinal cancer. The serum samples of healthy individuals and those of pancreatic cancer and colorectal cancer used for the measurement in Example 6 were analyzed using CA19-9 (manufactured by Tosoh Corporation, manufacturing/marketing notification number: 20400AMZ00913000) assay reagent, and the results are shown in FIG. 6. Further, the AUC values determined from the ROC analysis between the healthy group and the pancreatic cancer group or the colorectal cancer group, and P values in the significance test are shown in Table 7. CA19-9 showed a tendency for higher values in the pancreatic cancer group or the colorectal cancer group as compared to the healthy group, and the ROC analysis also showed that CA19-9 is an excellent gastrointestinal tumor marker. On the other hand, it has been shown that the iGDPP or tGDPP exhibits a better performance in the detection of pancreatic cancer and colorectal cancer, as compared to CA19-9.

TABLE 7

|  | Pancreatic cancer | | | Colorectal cancer | | |
| --- | --- | --- | --- | --- | --- | --- |
|  | iGDPP | tGDPP | CA19-9 | iGDPP | tGDPP | CA19-9 |
| AUC | 1.00 | 0.99 | 0.85 | 0.99 | 0.98 | 0.75 |
| Standard error | 0.00 | 0.01 | 0.08 | 0.01 | 0.02 | 0.08 |
| 95% confidence interval | 1.00 to 1.00 | 0.98 to 1.01 | 0.69 to 1.01 | 0.97 to 1.01 | 0.94 to 1.01 | 0.59 to 0.91 |
| P value | <0.0001 | <0.0001 | <0.0001 | <0.0001 | <0.0001 | <0.0026 |

<Example 8> Calculation of Sensitivity and Specificity of iGDPP, tGDPP and CA19-9

The sensitivity and the specificity of each of the markers were calculated using the results of the ROC analysis of iGDPP, tGDPP and CA19-9 shown in Examples 6 and 7. The values of the sensitivity and the specificity determined from the maximum value of Youden Index (sensitivity−(100−specificity)) as well as the cutoff value for each marker are shown in Table 8. Both the sensitivity and the specificity of iGDPP and tGDPP were 85% or greater in lung cancer, pancreatic cancer and colorectal cancer, revealing an excellent cancer detection performance of iGDPP and tGDPP. It has also been shown that iGDPP and tGDPP exhibit a better performance in the detection of pancreatic cancer and colorectal cancer, as compared to CA19-9. Further, it has been shown that iGDPP and tGDPP are capable of detecting three out of three cases of CA19-9-negative pancreatic cancer samples, and six out of eight cases of CA19-9-negative colorectal cancer samples, as positive.

TABLE 8

|  |  | Cutoff value | Sensitivity (%) | Specificity (%) |
| --- | --- | --- | --- | --- |
| Lung cancer | iGDPP | 0.19 | 88.9 | 96.7 |
|  | tGDPP | 0.59 | 94.4 | 95.0 |
| Pancreatic cancer | iGDPP | 0.26 | 100.0 | 100.0 |
|  | tGDPP | 0.59 | 100.0 | 95.0 |
|  | CA19-9 | 51.70 | 83.3 | 100.0 |
| Colorectal cancer | iGDPP | 0.23 | 87.5 | 100.0 |
|  | tGDPP | 0.55 | 93.8 | 90.0 |
|  | CA19-9 | 46.10 | 50.0 | 100.0 |
| Breast cancer | iGDPP | 0.22 | 63.6 | 100.0 |
|  | tGDPP | 0.41 | 90.9 | 66.7 |

<Example 9> Measurement of Clinical Samples (Esophageal Cancer, Stomach Cancer, Non-Small Cell Lung Cancer and Small Cell Lung Cancer)

The details of the serum sample panel (total of 120 cases) used in the present Example are shown in Table 9. The serum samples of healthy individuals were purchased from BioreclamationIVT, and various cancer serum samples were purchased from PROMEDDX or BioreclamationIVT. It is clearly described in the documents attached to the products of both companies, that these samples were collected in accordance with the protocols approved by the ethics committee.

TABLE 9

|  | Male | | | Female | |
| --- | --- | --- | --- | --- | --- |
|  | Number of samples | Number of samples | Age | Number of samples | Age |
| Healthy individuals | 60 | 30 | 62 ± 3.0 | 30 | 62 ± 1.6 |
| Esophageal cancer | 13 | 12 | 68 ± 9.9 | 1 | 54 |
| Stomach cancer | 17 | 11 | 67 ± 9.5 | 6 | 72 ± 5.2 |
| Non-small cell lung cancer | 20 | 9 | 69 ± 3.2 | 11 | 69 ± 8.2 |
| Small cell lung cancer | 10 | 5 | 67 ± 9.9 | 5 | 71 ± 6.2 |
| Total number of samples | 120 |  |  |  |  |

Figure 7:
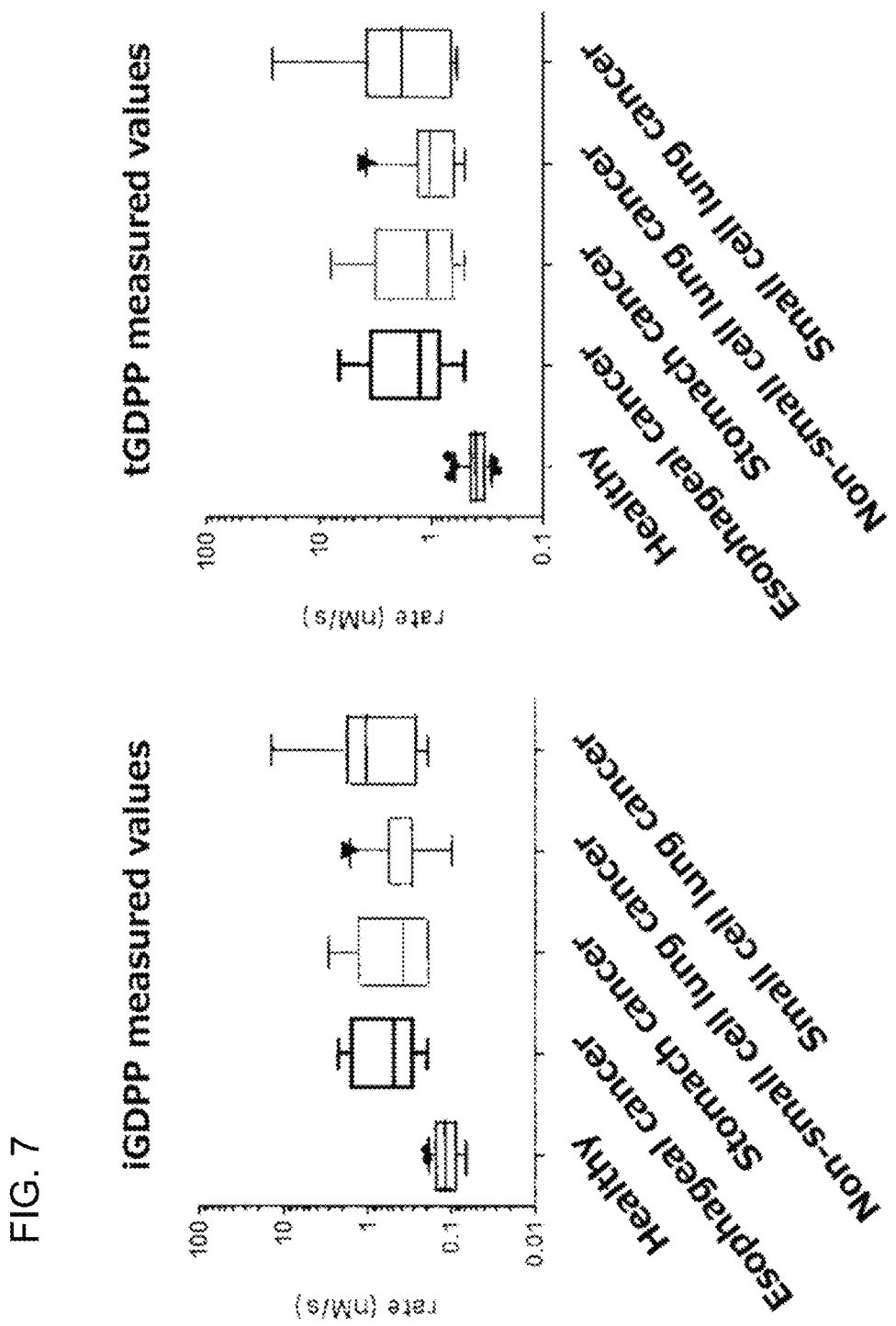
FIG. 7 is a diagram showing box plots of the measured values of iGDPP and tGDPP in samples of healthy individuals, and in samples of esophageal cancer, stomach cancer, non-small cell lung cancer and small cell lung cancer.

Using a fully automatic enzyme immunoassay apparatus AIA-2000 (manufactured by Tosoh Corporation) as an apparatus for the evaluation, the clinical samples were measured using the iGDPP and tGDPP assay reagents prepared in Example 3. The box plots of various measured values are shown in FIG. 7, and the minimum value, the 25 percentile, the median value, the 75 percentile, the maximum value, and the range of measured values in the 95% confidence interval, of the measured values of iGDPP and tGDPP in each of the sample groups, are shown in Table 10. The measured values of iGDPP and tGDPP were clearly higher in all of the esophageal cancer, stomach cancer, non-small cell lung cancer and small cell lung cancer groups, as compared to the healthy group.

TABLE 10

|  | Healthy individuals | Esophageal cancer | Stomach cancer | Non-small cell lung cancer | Small cell lung cancer |
|---|---|---|---|---|---|
| iGDPP measured values ||||||
| Minimum value | 0.07 | 0.16 | 0.17 | 0.10 | 0.21 |
| 25 percentile | 0.09 | 0.34 | 0.23 | 0.25 | 0.25 |
| Median value | 0.12 | 0.53 | 0.40 | 0.33 | 1.13 |
| 75 percentile | 0.16 | 1.56 | 1.28 | 0.54 | 1.82 |
| Maximum value | 0.21 | 2.30 | 3.01 | 1.66 | 14.57 |
| 95% confidence interval | 0.12–0.14 | 0.40–1.26 | 0.36–1.13 | 0.29–0.64 | –0.74–5.47 |
| tGDPP measured values ||||||
| Minimum value | 0.26 | 0.49 | 0.49 | 0.45 | 0.61 |
| 25 percentile | 0.34 | 0.88 | 0.67 | 0.63 | 0.70 |
| Median value | 0.40 | 1.32 | 1.13 | 1.03 | 1.92 |
| 75 percentile | 0.45 | 3.49 | 3.28 | 1.37 | 3.85 |
| Maximum value | 0.72 | 6.75 | 7.92 | 3.95 | 26.99 |
| 95% confidence interval | 0.39–0.44 | 0.95–3.52 | 1.00–3.33 | 0.83–1.61 | –1.086–10.33 |

The AUC values calculated from the ROC curve analysis of iGDPP and tGDPP between the group of healthy individuals and each of the esophageal cancer, stomach cancer, non-small cell lung cancer and small cell lung cancer groups, and the P values in the significance test are shown in Table 11. In each of all of the cancer types, iGDPP and tGDPP showed an AUC value of 0.9 or greater, and a statistically significant difference was observed. This has revealed an excellent cancer detection performance of iGDPP and tGDPP.

TABLE 11

|  | Esophageal cancer | | Stomach cancer | | Non-small cell lung cancer | | Small cell lung cancer | |
|---|---|---|---|---|---|---|---|---|
|  | iGDPP | tGDPP | iGDPP | tGDPP | iGDPP | tGDPP | iGDPP | tGDPP |
| AUC | 0.98 | 0.98 | 0.97 | 0.97 | 0.94 | 0.97 | 1.00 | 0.99 |
| Standard error | 0.02 | 0.01 | 0.02 | 0.02 | 0.04 | 0.02 | 0.00 | 0.01 |
| 95% confidence interval | 0.94 to 1.01 | 0.96 to 1.01 | 0.93 to 1.01 | 0.94 to 1.01 | 0.85 to 1.02 | 0.94 to 1.00 | 0.99 to 1.00 | 0.97 to 1.01 |
| P value | <0.0001 | <0.0001 | <0.0001 | <0.0001 | <0.0001 | <0.0001 | <0.0001 | <0.0001 |

<Example 10> Calculation of Sensitivity and Specificity of iGDPP and tGDPP in Esophageal cancer, Stomach cancer, Non-small Cell Lung Cancer and Small Cell Lung Cancer The sensitivity and the specificity of each of the markers were calculated using the results of the ROC curve analysis of iGDPP and tGDPP shown in Example 9. The values of the sensitivity and the specificity determined from the maximum value of Youden Index (sensitivity–(100–specificity)) as well as the cutoff value for each marker are shown in Table 12. Both the sensitivity and the specificity of iGDPP and tGDPP were 85% or greater in esophageal cancer, stomach cancer, non-small cell lung cancer and small cell lung cancer groups (excluding the sensitivity of iGDPP in stomach cancer), revealing an excellent cancer detection performance of iGDPP and tGDPP.

TABLE 12

|  |  | Cutoff value | Sensitivity (%) | Specificity (%) |
|---|---|---|---|---|
| Esophageal cancer | iGDPP | 0.25 | 92.3 | 100.0 |
|  | tGDPP | 0.60 | 92.3 | 95.0 |
| Stomach cancer | iGDPP | 0.22 | 82.4 | 100.0 |
|  | tGDPP | 0.58 | 88.2 | 95.0 |
| Non-small cell lung cancer | iGDPP | 0.20 | 90.0 | 96.7 |
|  | tGDPP | 0.59 | 90.0 | 95.0 |
| Small cell lung cancer | iGDPP | 0.20 | 100.0 | 96.7 |
|  | tGDPP | 0.59 | 100.0 | 95.0 |

Figure 8:
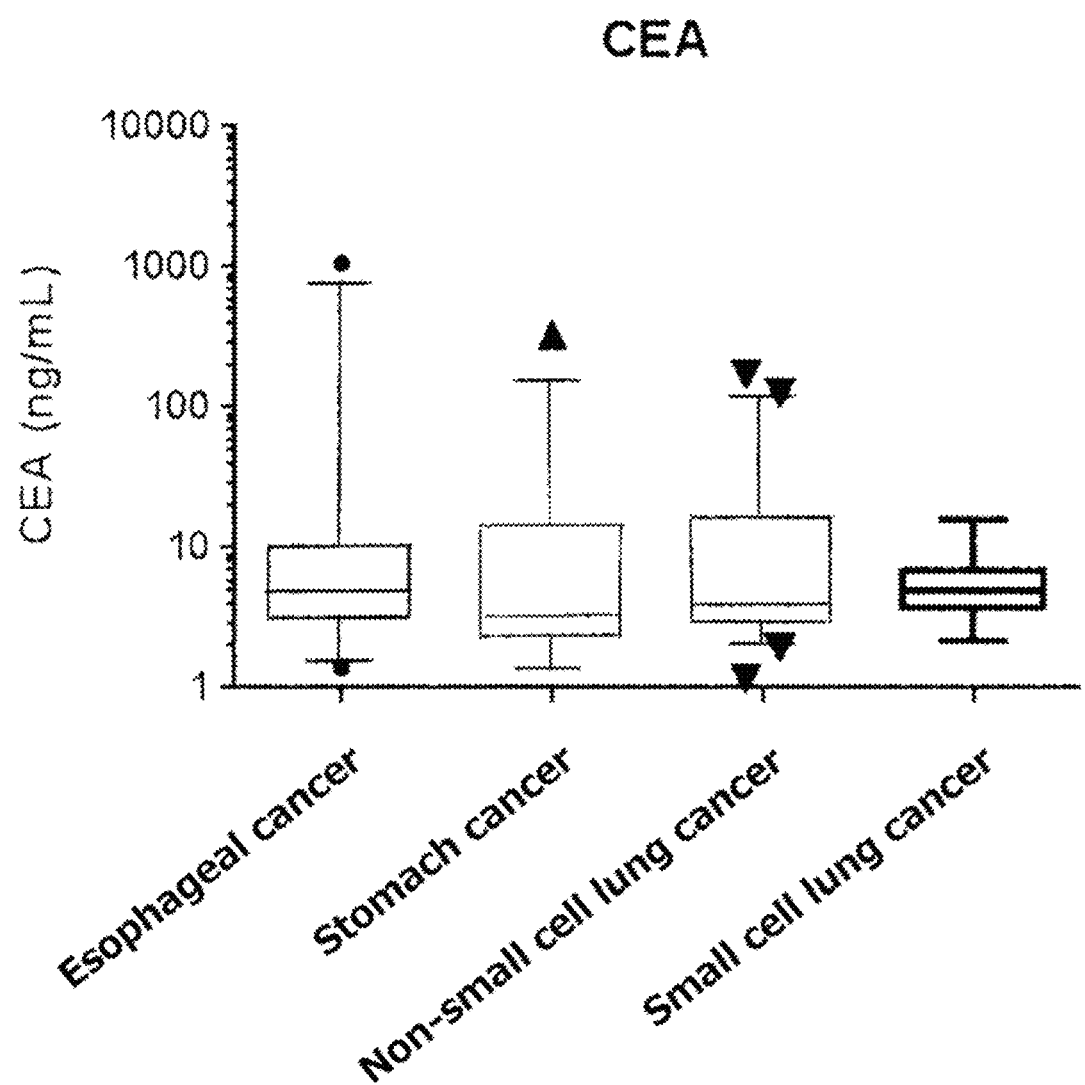
FIG. 8 is a diagram showing box plots of the measured values of CEA in the samples of esophageal cancer, stomach cancer, non-small cell lung cancer and small cell lung cancer.

<Example 11> Comparison of Positive Rates of iGDPP, tGDPP and CEA in Esophageal Cancer, Stomach Cancer, Non-small Cell Lung Cancer and Small Cell Lung Cancer The positive rate of CEA, which is a representative marker for cancer, in general, was compared with those of iGDPP and tGDPP, in esophageal cancer, stomach cancer, non-small cell lung cancer and small cell lung cancer. The samples of esophageal cancer, stomach cancer, non-small cell lung cancer and small cell lung cancer described in Example 9 were analyzed using a CEA assay reagent (manufactured by Tosoh Corporation, manufacturing/marketing notification number: 20100EZZ00112000). The positive rate of CEA was calculated using a cutoff value of 5 ng/mL or more, and the positive rates of iGDPP and tGDPP were calculated using cutoff values described in Example 10. The box plots of the measured values of CEA are shown in FIG. 8, and the list of positive rates are shown in Table 13. Although CEA showed a tendency for higher values in various cancer types, iGDPP and tGDPP showed a positive rate about two times higher than that of CEA in all of the esophageal cancer, stomach cancer, non-small cell lung cancer and small cell lung cancer groups, revealing an excellent cancer detection performance of iGDPP and tGDPP.

TABLE 13

|  | Esophageal cancer (Cutoff value) | Stomach cancer (Cutoff value) | Non-small cell lung cancer (Cutoff value) | Small cell lung cancer (Cutoff value) |
|---|---|---|---|---|
| CEA | 46.2 (5 ng/mL) | 41.2 (5 ng/mL) | 45.0 (5 ng/mL) | 50.0 (5 ng/mL) |
| iGDPP | 92.3 (0.25 nM/s) | 82.4 (0.22 nM/s) | 90.0 (0.20 nM/s) | 100.0 (0.20 nM/s) |
| tGDPP | 92.3 (0.60 nM/s) | 82.4 (0.58 nM/s) | 90.0 (0.59 nM/s) | 100.0 (0.59 nM/s) |

Figure 9:
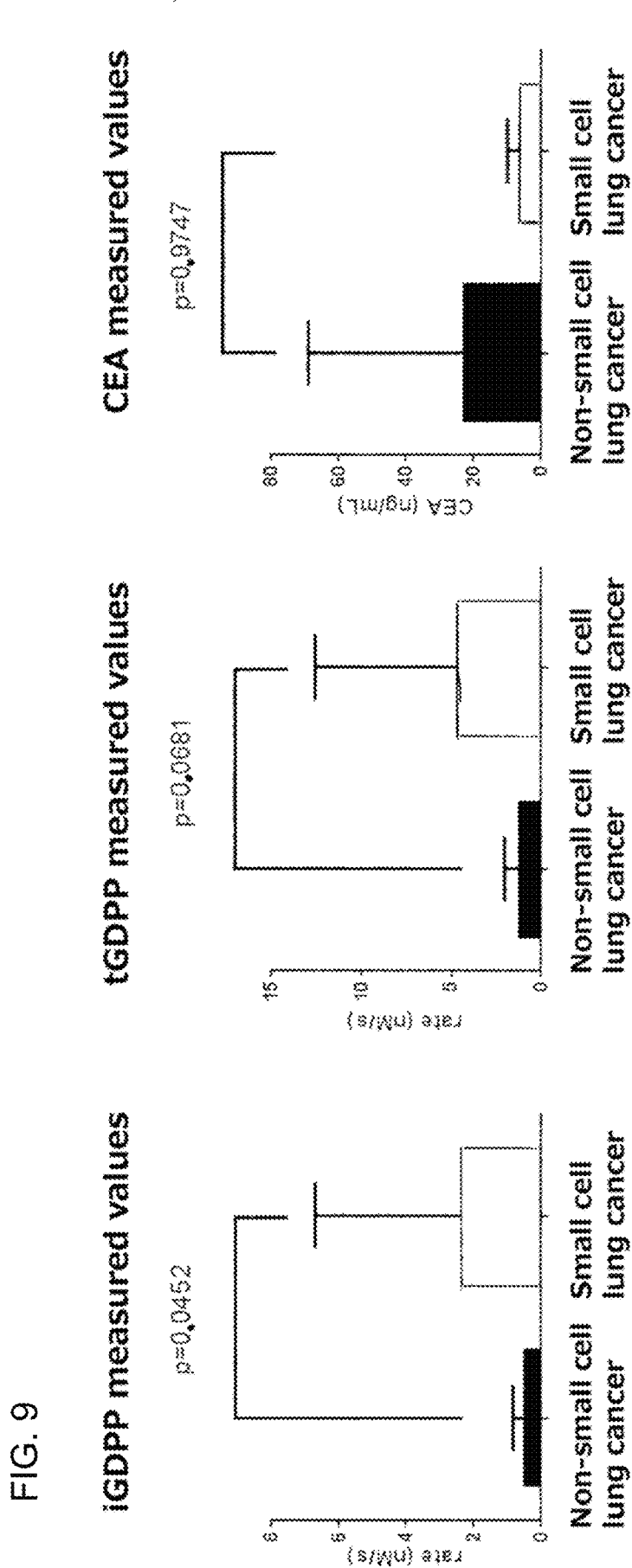
FIG. 9 is a diagram comparing the measured values of iGDPP, tGDPP and CEA in the samples of non-small cell lung cancer and small cell lung cancer.
Figure 10:
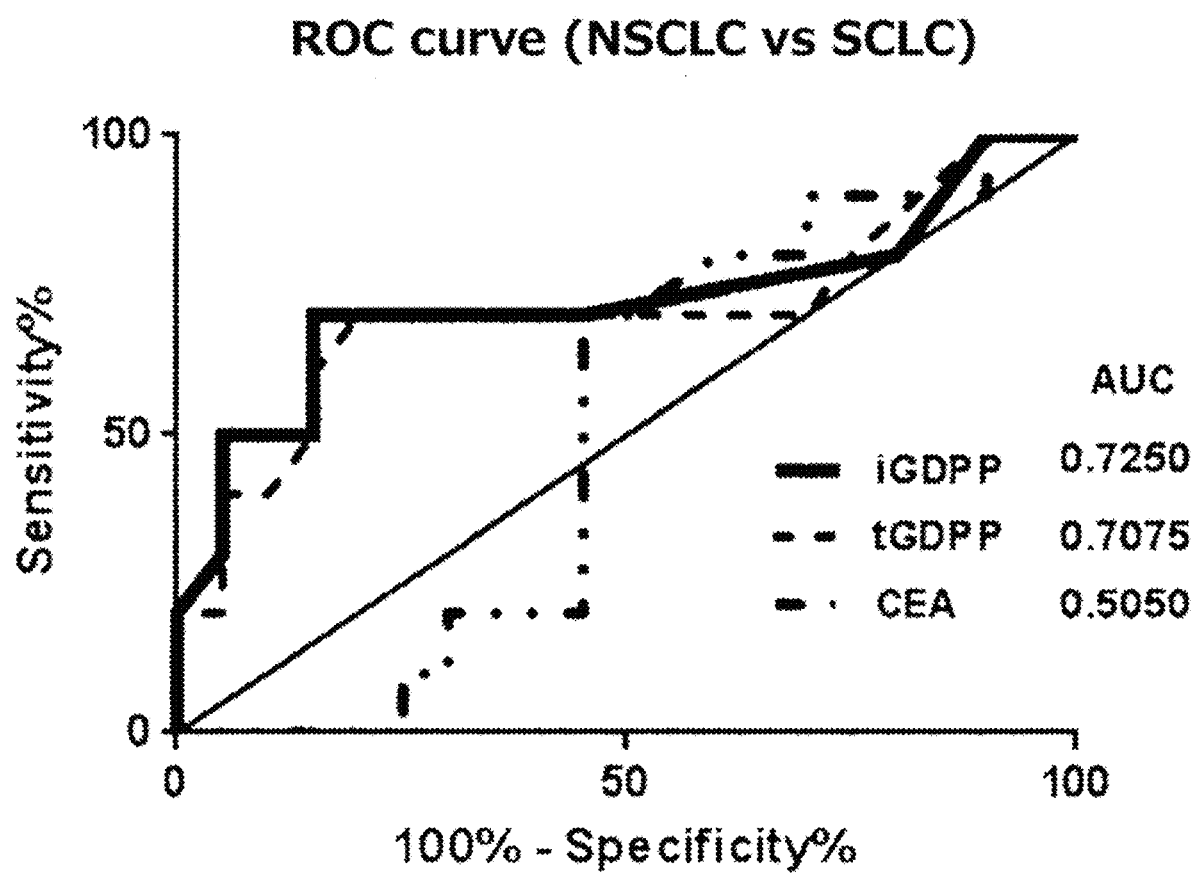
FIG. 10 is a diagram showing the results of the ROC curve analysis of iGDPP, tGDPP and CEA in the samples of non-small cell lung cancer and small cell lung cancer.

<Example 12> Comparison of Ability for Distinguishing Tissue Types in Lung Cancer Between iGDPP, tGDPP and CEA The tissue types of lung cancer are mainly classified into non-small cells (about 85%) and small cells (about 15%). Since the treatment plan varies depending on the tissue type, it is considered important to distinguish between the tissue types. Therefore, the ability for distinguishing the tissue type of small cell lung cancer from that of non-small cell lung cancer was compared between iGDPP, tGDPP and CEA. The results of the comparative analysis between CEA, iGDPP and tGDPP in the group of non-small cell lung cancer samples or the group of small cell lung cancer samples are shown in FIG. 9, and the results of the ROC curve analysis are shown in FIG. 10. CEA showed a tendency for higher values in non-small cell lung cancer, but no significant difference was observed (Mann Whitney's U test, p=0.9747). On the other hand, iGDPP and tGDPP showed a tendency for higher values in small cell lung cancer, and a significant difference was observed in iGDPP (Mann Whitney's U test, p=0.0452). In the ROC curve analysis, CEA had an AUC value of 0.5, and it has been shown that CEA has no distinguishing ability. On the other hand, iGDPP and tGDPP showed an AUC value of about 0.7, and it has been shown that iGDPP and tGDPP have a good distinguishing ability.

The present invention has been described in detail, with reference to specific embodiments. It will be apparent to those skilled in the art that various modifications and alterations can be made without departing from the spirit and scope of the invention.

Note that, the entire contents of the specification, sequence listing, claims, drawings and abstract of Japanese Patent Application No. 2017-165409, filed on Aug. 30, 2017 are cited and incorporated herein as the disclosure of the specification of the present invention.

INDUSTRIAL APPLICABILITY

The present invention provides a method and a reagent for detecting GDF15 propeptide, which enables to detect one or more selected from the group consisting of lung cancer, pancreatic cancer, colorectal cancer, breast cancer, esophageal cancer and stomach cancer, or to distinguish and to detect non-small cell lung cancer and small cell lung cancer. The above described method and reagent enable a simple and highly accurate detection, by blood diagnosis or the like, of various types of cancer which have been difficult to be identified by a conventional marker. As a result, they allow for a simple detection of cancer, making it possible to select treatment methods and to determine therapeutic effects, and thus are extremely useful industrially.

The invention claimed is:

1. A method of detecting the intact growth and differentiation factor 15 (GDF15) propeptide level in a sample of a subject having cancer, the method comprising:
   measuring the intact GDF15 propeptide level in the sample, and
   comparing the intact GDF15 propeptide level obtained by the measurement with a reference value calculated from a control,
   wherein the intact GDF15 propeptide consists of the amino acid sequence from the leucine at the 30th residue to the arginine at the 194th residue in the GDF15 amino acid sequence of SEQ ID NO:2, and
   wherein the cancer is one or more selected from the group consisting of stomach cancer, pancreatic cancer, colorectal cancer, lung cancer, breast cancer, esophageal cancer, non-small cell lung cancer, and small cell lung cancer.

2. A method of detecting a level of a fragment of intact growth and differentiation factor 15 (GDF15) propeptide (GDF15 propeptide fragment) in a sample of a subject having cancer, the method comprising:
   measuring the GDF15 propeptide fragment level in the sample, and
   comparing the GDF15 propeptide fragment level obtained by the measurement with a reference value calculated from a control, wherein the intact GDF15 propeptide consists of the amino acid sequence from the leucine at the 30th residue to the arginine at the 194th residue in the GDF15 amino acid sequence of SEQ ID NO:2, wherein the GDF15 propeptide fragment is selected from the group consisting of the following GDF15 propeptide fragment (A) and the following GDF15 propeptide fragment (B):

(A) a GDF15 propeptide fragment having the following properties:

contains an amino acid sequence from the lysine at the 58th residue to at least the aspartic acid at the 167th residue in the GDF15 amino acid sequence of SEQ ID NO:2;

(B) a GDF15 propeptide fragment having the following properties:

contains an amino acid sequence from the glutamic acid at the 74th residue to at least the aspartic acid at the 167th residue in the GDF15 amino acid sequence of SEQ ID NO:2, and wherein the cancer is one or more selected from the group consisting of stomach cancer, pancreatic cancer, colorectal cancer, lung cancer, breast cancer, esophageal cancer, non-small cell lung cancer, and small cell lung cancer.

3. A method of detecting the total level of intact growth and differentiation factor 15 (GDF15) propeptide and a fragment of the intact GDF15 propeptide (GDF15 propeptide fragment) in a sample of a subject having cancer, the method comprising:

measuring the intact GDF15 propeptide level and the GDF15 propeptide fragment level in the sample, and comparing the intact GDF15 propeptide level and the GDF15 propeptide fragment level obtained by the measurement with a reference value calculated from a control, wherein the intact GDF15 propeptide consists of the amino acid sequence from the leucine at the 30th residue to the arginine at the 194th residue in the GDF15 amino acid sequence of SEQ ID NO:2, wherein the GDF15 propeptide fragment is selected from the group consisting of the following GDF15 propeptide fragment (A) and the following GDF15 propeptide fragment (B):

(A) a GDF15 propeptide fragment having the following properties:

contains an amino acid sequence from the lysine at the 58th residue to at least the aspartic acid at the 167th residue in the GDF15 amino acid sequence of SEQ ID NO:2;

(B) a GDF15 propeptide fragment having the following properties:

contains an amino acid sequence from the glutamic acid at the 74th residue to at least the aspartic acid at the 167th residue in the GDF15 amino acid sequence of SEQ ID NO:2, and wherein the cancer is one or more selected from the group consisting of stomach cancer, pancreatic cancer, colorectal cancer, lung cancer, breast cancer, esophageal cancer, non-small cell lung cancer, and small cell lung cancer.

4. The method according to claim 1, wherein the measurement is carried out by an antigen-antibody reaction using an antibody that recognizes GDF15 propeptide.

5. The method according to claim 1, wherein the measurement is carried out using mass spectrometry.

6. The method according to claim 2, wherein the measurement is carried out by an antigen-antibody reaction using an antibody that recognizes GDF15 propeptide.

7. The method according to claim 2, wherein the measurement is carried out using mass spectrometry.

8. The method according to claim 3, wherein the measurement is carried out by an antigen-antibody reaction using an antibody that recognizes GDF15 propeptide.

9. The method according to claim 3, wherein the measurement is carried out using mass spectrometry.

* * * * *